US007794976B2

(12) United States Patent
Handa et al.

(10) Patent No.: US 7,794,976 B2
(45) Date of Patent: Sep. 14, 2010

(54) METHODS AND MATERIALS FOR EXPRESSION OF A RECOMBINANT PROTEIN

(75) Inventors: Masahisa Handa, Berkeley, CA (US); Arnold H. Horwitz, San Leandro, CA (US); Robyn Cotter, Oakland, CA (US); Eddie Batista, San Francisco, CA (US)

(73) Assignee: XOMA Technology Ltd., Berkeley, CA (US)

( * ) Notice: Subject to any disclaimer, the term of this patent is extended or adjusted under 35 U.S.C. 154(b) by 10 days.

(21) Appl. No.: 11/831,691

(22) Filed: Jul. 31, 2007

(65) Prior Publication Data

US 2008/0145894 A1  Jun. 19, 2008

Related U.S. Application Data

(63) Continuation of application No. 11/295,006, filed on Dec. 5, 2005, now abandoned.

(60) Provisional application No. 60/633,056, filed on Dec. 3, 2004.

(51) Int. Cl.
*C12P 21/04* (2006.01)
*C12N 15/00* (2006.01)
*C12N 5/12* (2006.01)

(52) U.S. Cl. .................. 435/69.1; 435/320.1; 435/326; 435/327; 435/70.1; 536/23.1; 536/23.53; 530/387.3

(58) Field of Classification Search ........................ None
See application file for complete search history.

(56) References Cited

U.S. PATENT DOCUMENTS

| 5,149,635 | A  | * | 9/1992  | Gillies ........................ 435/69.1 |
| 6,472,585 | B1 | * | 10/2002 | Botstein et al. ............... 800/18 |
| 6,500,641 | B1 |   | 12/2002 | Chen et al. |
| 7,005,413 | B1 | * | 2/2006  | Boyle et al. ..................... 514/2 |
| 2006/0121604 | A1 | | 6/2006 | Handa et al. |
| 2008/0124762 | A1 | | 5/2008 | Handa et al. |

FOREIGN PATENT DOCUMENTS

| EP | 0292879 A2 | 11/1988 |
| WO | 2004053137 A2 | 6/2004 |

OTHER PUBLICATIONS

Xu et al. J Control Release. May 17, 2002;81(1-2):155-63.*
Bashaw et al. Replication from oriP of Epstein-Barr virus requires exact spacing of two bound dimers of EBNA1 which bend DNA. J Virol. Nov. 2001;75(22):10603-11.*
Yates et al. The minimal replicator of Epstein-Barr virus oriP. J Virol. May 2000;74(10):4512-22.*
Pham, et al. Large-scale transfection of mammalian cells for the fast production of recombinant protein. Molecular Biotechnology 34:225-237 (2006).
Thomas, et al. Enhancing polyethylenimine's delivery of plasmid DNA into mammalian cells. Proceedings of the National Academy of Sciences 99:14640-14645 (2002).
Oh, et al. Polyethylenimine-mediated cellular uptake, nucleus trafficking and expression of cytokine plasmid DNA. Gene Therapy 9:1627-1632 (2002).
Girard, et al. 100-liter transient transfection. Cytotechnology 38:15-21 (2002).
Gonzalez et al., "Kinetic Model of BiP- and PDI-mediated Protein Folding and Assembly", J. Theor. Biol. 214:529-537 (2002).
McLean, et al., "Human and murine immunoglobulin expression vector cassettes," Molecular Immunology, 37:837-845 (2000).
Rahman, et al., "Properties of Whole Human IgG Molecules Produced by the Expression of Cloned Anti-DNA Antibody cDNA in Mammalian Cells," Journal of Autoimmunity 11:661-669 (1998).
Biblia, et al., A Structured Model for Monoclonal Antibody Synthesis in Exponentially Growing and Stationary Phase Hybridoma Cells, Biotechnology and Bioengineering 37:210-226 (1991).
Carrier, et al., Investigating Autocatalytic Gene Expression Systems Through Mechanistic Modeling, J Theor. Bio. 201:25-36 (1991).
Hsu, et al., Coexpression of Molecular Chaperone BiP Improves Immunoglobulin Solubility and IgG Secretion from Trichoplusia ni Insect Cells, Biotechnol. Prog. 13:96-104 (1997).
Percy, et al., A Theoretical Model for the Covalent Assembly of Immunoglobulins, J Biological Chemistry 250 (6):2398-2400 (1975).
Shusta, et al., Increasting the secretory capacity of saccharomyces cerevisiae for production of single-chain antibody fragments, Nature Biotech. 16: 773-777 (1998).
Whiteley, et al., Modeling Assembly, Aggregation and Chaperoning of Immunoglobulin G Production in Insect Cells, Biotech. and Bioeng. 56: 106-116 (1997).
Boshart et al., "A Very Strong Enhancer is Located Upstream of an Immediate Early Gene of Human Cytomeglalovirus", Cell, 41:521-530 (1985).
Boussif et al., "A versatile vector for gene and oglionucleotide transfer into cells in culture and in vivo: Polyethylenimine", Proc. Natl. Acad. Sci., 92:7297-7301 (1995).
Bruce et al., "Dialysis-based bioreactor systems for the production of monoclonal antibodies—alternatives to ascites production in mice"; J. Immunol. Methods, 264(1-2):59-68 (2002).

(Continued)

*Primary Examiner*—Zachariah Lucas
*Assistant Examiner*—Michelle Horning
(74) *Attorney, Agent, or Firm*—John M. Polo

(57) ABSTRACT

Recombinant expression vectors are provided comprising a 3'UTR of a light chain and an Epstein-Barr virus origin of replication. Also provided are host cells comprising such vectors and methods of producing recombinant protein with such vectors. Additional methods of producing a recombinant protein involve contacting cells with a first and second vector, each of which encode a different polypeptide chain, and wherein the second vector is present in an amount which is about 1.5 to 2.5 times as much as that of the first vector. Cells also can be transfected with a recombinant transient expression vector encoding a protein and are cultured in a medium in a membrane-enhanced culturing vessel to produce recombinant protein.

36 Claims, 18 Drawing Sheets

OTHER PUBLICATIONS

Cachianes G. et al., "Epstein-Barr virus-derived vectors for transient and stable expression of recombinant proteins"; Biotechniques, Informa Life Sciences Publishing, vol. 15 (2):255, 256, 258 (1993).

CELLine, "Efficient Expression of Recombinant Proteins", IBS Integra Biosciences, 1-6 (downloaded/printed Nov. 30, 2004).

Cote et al., "Serum-Free Production of Recombinant Proteins and Adenoviral Vectors by 293SF-3F6 Cells", Biotechnol. Bioeng., 59(5):567-575 (1998).

Durocher et al., "High level and high throughput recombinant protein production by transient transfection of suspension-growing 293EBNA1 cells", Nucleic Acids Res., 30(2):1-9 (2002).

Kim Seon-Young, et al., Journal of Biotechnology, "The human Elongation factor 1 alpha (EF-1alpha) first intron highly enhances expression of foreign genes from the murine cytomegalovirus promoter", 93(2):183-187 (2002).

Langle-Rouault F, et al., "Up to 100 Fold Increase of Apparent Gene Expression in the Presence of Epstein-Barr Virus oriP Sequences and EBNI-1: Implications of the Nuclear Import of Plasmids", Journal of Virology, The American Society for Microbiology, 72(7): 6181-6185 (1998).

Matsumoto and Studer, "Continuous Recombinant Protein Production in Baculovirus Infected SF9 Cells Using CELLine Classic 1000 Two-Compartment Bioreactors", IBS Integra Biosciences Application Note, 1-2 (PDF created Jul. 15, 2004).

Meissner et al., Biotechnol. Bioeng.- Combinatorial Chemistry, "Transient gene expression: Recombinant protein production with suspension-adapted HEK293-EBNA cells"; Wiley, New York 197-203 (2001).

Mislick et al., "Evidence for the role of proteaglycans in cation-mediated gene transfer", Proc. Natl. Acad. Sci., 93: 12349-12354 (1996).

Mittermaier and Zang-Gandor, "Long-Term High Level Protein Expression in Adherent, Protein-free Growing BHK Cells Using INTEGRA CELLine adhere using 1000 Bioreacter Flasks", IBS Integra Biosciences Application Note, 1-2 (PDF created Oct. 30, 2003).

Nagel et al., "Membrane based cell culture systems—an alternative to in vivo production of monoclonal antibodies," 4 pgs. (PDF created Mar. 30, 2003).

Reisman et al., "A Putative Origin of Replication of Plasmids Derived from Epstein-Barr Virus is Composed of Two cis-Acting Components", Mol. Cell. Biol., 5:1822-1832 (1985).

Scott et al., "Manufacture of Pure Monoclonal Antibodies by Heterogeneous Culture Without Downstream Purification", BioTechniques, 31(3):666-668 (2001).

"Building a Better Mousetrap: INTEGRA Biosciences CELLine", The Scientist, 12(8):15 (1998).

Trebak et al., "Efficient laboratory scale production of monoclonal antibodies using membrane-based high-density cell culture technology", Journal of Immunological Methods, 230:59-70 (1999).

Wolf, "Comparison of batch versus CELLine culture for production of monoclonal antibody in vitro as alternatives to ascites. Application: Murine Hybridoma", Integra CELLine Technical Report II, 1-5 (PDF created Nov. 9, 1998).

Wolf, "Antibody Manufacture in the CELLine CL1000. Application: Murine Hybridoma", Integra CELLine Technical Report III, 1-6 (PDF created Nov. 9, 1998).

Wolf, "High Density Suspension Culture for Recombinant Protein Production from CHO Cells", Integra CELLine Technical Report VI, 1-5 (PDF created Oct. 9, 1999).

Wright J. L. et al., Journal of Biotechnology, "Transfection of partially purified plasmid DNA for high level transient protein expression in HEK293-EBNA cells", 102(3): 211-221 (2003).

Wurm et al., "Large-scale transient expression in mammalian cells for recombinant protein production", Curr. Opn. Biotech., 10:156-159 (1999).

Xu et al., "Transcription Termination and Chromatin Structure of the Active Immunoglobulin k Gene Locus", J. Biol. Chem., 26(8)1:3838-3845 (1986).

Gonzalez et al., "Kinetic Model of BiP- and PDI-mediated Protein Folding and Assembly", J. Theor. Biol. 214:529-537 (2002).

McLean, et al., "Human and murine immunoglobulin expression vector cassettes," Molecular Immunology, 37:837-845 (2000).

Rahman, et al., "Properties of Whole Human IgG Molecules Produced by the Expression of Cloned Anti-DNA Antibody cDNA in Mammalian Cells," Journal of Autoimmunity 11:661-669 (1998).

PCT International Search Report, mailed Nov. 14, 2006, PCT/US2005/043922.

USPTO Non-Final Office Action mailed Jan. 25, 2010 for U.S. Appl. 11/831,882.

Fitzgerald, et al., Pharmacological and Biochemical Characterization of Recombinant Human Galanin GALR1 Receptor: Agonist Character of Chimeric Galanin Peptides, Journal of Pharmacology and Experimental Therapeutics 287(2): 448-456 (1998).

* cited by examiner

FIGURE 10

SEQ ID NO: 1

HindIII
```
   1 AAGCTTGAGT TTTATGGGTG GCAGTCACTG GCTGGCTAGG CACATAGCCA GGCCAAACCT AGGCCTCCAA
  71 GGGCTCCCCA AAATCTGAAT TTCTGAGTAG TCTTCATCCC CTCTCCTGCT CTAAGGTCAG GTCCATCCTC
 141 TCTGGTCCTT ACCTTGATGA CAAGGATCGA CATTGATTAT TGACTAGTTA TTAATAGTAA TCAATTACGG
 211 GGTCATTAGT TCATAGCCCA TATATGGAGT TCCGCGTTAC ATAACTTACG GTAAATGGCC CGCCTGGCTG
 281 ACCGCCCAAC GACCCCCGCC CATTGACGTC AATAATGACG TATGTTCCCA TAGTAACGCC AATAGGGACT
 351 TTCCATTGAC GTCAATGGGT GGAGTATTTA CGGTAAACTG CCCACTTGGC AGTACATCAA GTGTATCATA
 421 TGCCAAGTAC GCCCCCTATT GACGTCAATG ACGGTAAATG GCCCGCCTGG CATTATGCCC AGTACATGAC
 491 CTTATGGGAC TTTCCTACTT GGCAGTACAT CTACGTATTA GTCATCGCTA TTACCATGGT GATGCGGTTT
 561 TGGCAGTACA TCAATGGGCG TGGATAGCGG TTTGACTCAC GGGGATTTCC AAGTCTCCAC CCCATTGACG
 631 TCAATGGGAG TTTGTTTTGG CACCAAAATC AACGGGACTT TCCAAAATGT CGTAACAACT CCGCCCCATT
 701 GACGCAAATG GGCGGTAGGC GTGTACGGTG GAGGTCTAT ATAAGCAGAG CTCGTTTAGT GAACCGTCAG
 771 ATCGCCTGGA GACGCCATCC ACGCTGTTTT GACCTCCATA GAAGACACCG GGACCGATCC AGCCTCCGCG
 841 GCCGGGAACG GTGCATTGGA ACGCGGATTC CCCGTGCCAA GAGTGACGTA AGTACCGCCT ATAGAGTCTA
 911 TAGGCCCACC CCCTTGGCTT CTTATGGATC CGGTGGTGGT GCAAATCAAA GAACTGCTCC TCAGTGGATG
```
                                                                    SalI     EcoRI
```
 981 TTGCCTTTAC TTCTAGGCCT GTACGGAAGT GTTACTTCTG CTCTAAAAGC TGCTGCAGGT CGACGAATTC
```

ClaI    EcoRV    XhoI
```
1051 ATCGATGATA TCTCGAGCCC GCCCGTCACA AAGAGCTTCA ACAGGGGAGA GTGTTAGAGG
1111 GAGAAGTGCC CCCACCTGCT CCTCAGTTCC AGCCTGACCC CCTCCCATCC TTTGGCCTCT GACCCTTTTT
1181 CCACAGGGGA CCTACCCCTA TTGCGGTCCT CCAGCTCATC TTTCACCTCA CCCCCCTCCT CCTCCTTGGC
1251 TTTAATTATG CTAATGTTGG AGGAGAATGA ATAAATAAAG TGAATCTTTG CACCTGTGGT TTCTCTCTTT
1321 CCTCACTAGA GGATCTCTGT CTTTCTTACT AAATGGTAGT AATCAGTTGT TTTTCCAGTT ACCTGGGTTT
1391 CTCTTCTAAA GAAGTTAAAT GTTTAGTTGC CCTGAAATCC ACCACACTTA AAGGATAAAT AAAACCCTCC
1461 ACTTGCCCTG GTTGGCTGTC CACTACATGG CAGTCCTTTC TAAGGTTCAC GAGTACTATT CATGGCTTAT
1531 TTCTCTGGGC CATGGTAGGT TTGAGGAGGC ATACTTCCTA GTTTTCTTCC CCTAAGTCGT CAAAGTCCTG
1601 AAGGGGGACA GTCTTTACAA GCACATGTTC TGTAATCTGA TTCAACCTAC CCAGTAAACT TGGCGAAGCA
1671 GTAGAATCAT TATCACAGGA AGCAAAGGCA ACCTAAATGT GCAAGCAATA GGAAAATGTG GAAGCCCATC
1741 ATAGTACTTG GACTTCATCT GCTTTTGTGC CTTCACTAAG TTTTTAAACA TGAGCTGGCT CCTATCTGCC
1811 ATTGGCAAGG CTGGGCACTA CCCACAACCT ACTTCAAGGA CCTCTATACC GTGAGATTAC ACACATACAT
1881 CAAAATTTGG GAAAAGTTCT ACCAAGCTGA GAGCTGATCA CCCCACTCTT AGGTGCTTAT CTCTGTACAC
1951 CAGAAACCTT AAGAAGCAAC CAGTATTGAG AGACTCATTT ATGAAAGTCT AAAACTGGAT ACAACCAAAA
2021 TGTCCACCAA CAGTTAAATT ATGACATGTT CACAATTGAG CTATTACTTA ATAAGGAGAA TTAATAAAAT
2091 AAAACTTAAG AGCATAGTTT AATCTCATAA ACAAGATAAT AAGCAAAACA AAACATTTTT TCATCCATGT
2161 AAGTTTAAAA GCAGGTAAAA TTTAAAATTA AGAGAGACAT AAGTTTTGAG GTAGCAAGAT GGAAACTCTG
2231 GGGCTTGGGG AATGTTCTGT CTCTCTGTAT GGGATGTGAA AGTTACTATT GTGGAATTGG GATCTATGTT
2301 CTTCCTGTAT ATATTGTATA CTTCATAATA ACTTCACCTA AGAAATATC TAATACCCAG TGCATACATA
2371 AAAGAGGATA CAAGCAATGA ATCATACGTC AAGGCCAGAA AGACAATAAA GTAGGGATC CAGACATGAT
2441 AAGATACATT GATGAGTTTG GACAAACCAC AACTAGAATG CAGTGAAAAA AATGCTTTAT
2501 TTGTGAAATT TGTGATGCTA TTGCTTTATT TGTAACCATT ATAAGCTGCA ATAAACAAGT
```
     XbaI
```
2561 TctctagaTG TGTAACTCTT GGCTGAAGCT CTTACACCAA TGCTGGGGGA CATGTACCTC CCAGGGGCCC
2631 AGGAAGACTA CGGGAGGCTA CACCAACGTC AATCAGAGGG GCCTGTGTAG CTACCGATAA GCGGACCCTC
2701 AAGAGGGCAT TAGCAATAGT GTTTATAAGG CCCCCTTGTT AACCCTAAAC GGGTAGCATA TGCTTCCCGG
2771 GTAGTAGTAT ATACTATCCA GACTAACCCT AATTCAATAG CATATGTTAC CCAACGGGAA GCATATGCTA
2841 TCGAATTAGG GTTAGTAAAA GGGTCCTAAG GAACAGCGAT ATCTCCCACC CCATGAGCTG TCACGGTTTT
2911 ATTTACATGG GGTCAGGATT CCACGAGGGT AGTGAACCAT TTTAGTCACA AGGGCAGTGG CTGAAGATCA
2981 AGGAGCGGGC AGTGAACTCT CCTGAATCTT CGCCTGCTTC TTCATTCTCC TTCGTTTAGC TAATAGAATA
3051 ACTGCTGAGT TGTGAACAGT AAGGTGTATG TGAGGTGCTC GAAAACAAGG TTTCAGGTGA CGCCCCCAGA
3121 ATAAAATTTG GACGGGGGGT TCAGTGGTGG CATTGTGCTA TGACACCAAT ATAACCCTCA CAAACCCCTT
3191 GGGCAATAAA TACTAGTGTA GGAATGAATA ATTCTGAATA TCTTTAACAA TAGAAATCCA TGGGGTGGGG
3261 ACAAGCCGTA AAGACTGGAT GTCCATCTCA CACGAATTTA TGGCTATGGG CAACACATAA TCCTAGTGCA
3331 ATATGATACT GGGGTTATTA AGATGTGTCC CAGGCAGGGA CCAAGACAGG TGAACCATGT TGTTACACTC
3401 TATTTGTAAC AAGGGGAAAG AGAGTGGACG CCGACAGCAG CGGACTCCAC TGGTTGTCTC TAACACCCCC
3471 GAAAATTAAA CGGGGCTCCA CGCCAATGGG GCCCATAAAC AAAGACAAGT GGCCACTCTT TTTTTTGAAA
3541 TTGTGGAGTG GGGGCACGCG TCAGCCCCCA CACGCCGCCC TGCGGTTTTG GACTGTAAAA TAAGGGTGTA
3611 ATAACTTGGC TGATTGTAAC CCCGCTAACC ACTGCGGTCA AACCACTTGC CCACAAAACC ACTAATGGCA
3681 CCCCGGGGAA TACCTGCATA AGTAGGTGGG CGGGCCAAGA TAGGGGCGCG ATTGCTGCGA TCTGGAGGAC
3751 AAATTACACA CACTTGCGCC TGAGCGCCAA GCACAGGGTT GTTGGTCCTC ATATTCACGA GGTCGCTGAG
3821 AGCACGGTGG GCTAATGTTG CCATGGGTAG CATATACTAC CCAAATATCT GGATAGCATA TGCTATCCTA
3891 ATCTATATCT GGGTAGCATA GGCTATCCTA ATCTATATCT GGGTAGCATA TGCTATCCTA ATCTATATCT
```

FIGURE 10 (CONTINUED)

```
3961 GGGTAGTATA TGCTATCCTA ATTTATATCT GGGTAGCATA GGCTATCCTA ATCTATATCT GGGTAGCATA
4031 TGCTATCCTA ATCTATATCT GGGTAGTATA TGCTATCCTA ATCTGTATCC GGGTAGCATA TGCTATCCTA
4101 ATAGAGATTA GGGTAGTATA TGCTATCCTA ATTTATATCT GGGTAGCATA TACTACCCAA ATATCTGGAT
4171 AGCATATGCT ATCCTAATCT ATATCTGGGT AGCATATGCT ATCCTAATCT ATATCTGGGT AGCATAGGCT
4241 ATCCTAATCT ATATCTGGGT AGCATATGCT ATCCTAATCT ATATCTGGGT AGTATATGCT ATCCTAATTT
4311 ATATCTGGGT AGCATAGGCT ATCCTAATCT ATATCTGGGT AGCATATGCT ATCCTAATCT
4371 ATATCTGGGT AGTATATGCT ATCCTAATCT GTATCCGGGT AGCATATGCT ATCCTCATGC ATATACAGTC
4441 AGCATATGAT ACCCAGTAGT AGAGTGGGAG TGCTATCCTT TGCATATGCC GCCACCTCCC AAGGGGGCGT
                                                               SphI
4511 GAATTTTCGC TGCTTGTCCT TTTCCTGCTG GTTGGCATGC CGGGGAGAGG CGGTTTGCGT ATTGGGCGCT
4581 CTTCCGCTTC CTCGCTCACT GACTCGCTGC GCTCGGTCGT TCGGCTGCGG CGAGCGGTAT CAGCTCACTC
4651 AAAGGCGGTA ATACGGTTAT CCACAGAATC AGGGGATAAC GCAGGAAAGA ACATGTGAGC AAAAGGCCAG
4721 CAAAAGGCCA GGAACCGTAA AAAGGCCGCG TTGCTGGCGT TTTTCCATAG GCTCCGCCCC CCTGACGAGC
4791 ATCACAAAAA TCGACGCTCA AGTCAGAGGT GGCGAAACCC GACAGGACTA TAAAGATACC AGGCGTTTCC
4861 CCCTGGAAGC TCCCTCGTGC GCTCTCCTGT TCCGACCCTG CCGCTTACCG GATACCTGTC CGCCTTTCTC
4931 CCTTCGGGAA GCGTGGCGCT TTCTCATAGC TCACGCTGTA GGTATCTCAG TTCGGTGTAG GTCGTTCGCT
5001 CCAAGCTGGG CTGTGTGCAC GAACCCCCCG TTCAGCCCGA CCGCTGCGCC TTATCCGGTA ACTATCGTCT
5071 TGAGTCCAAC CCGGTAAGAC ACGACTTATC GCCACTGGCA GCAGCCACTG GTAACAGGAT TAGCAGAGCG
5141 AGGTATGTAG GCGGTGCTAC AGAGTTCTTG AAGTGGTGGC CTAACTACGG CTACACTAGA AGAACAGTAT
5211 TTGGTATCTG CGCTCTGCTG AAGCCAGTTA CCTTCGGAAA AAGAGTTGGT AGCTCTTGAT CCGGCAAACA
5281 AACCACCGCT GGTAGCGGTG GTTTTTTTGT TTGCAAGCAG CAGATTACGC GCAGAAAAAA AGGATCTCAA
5351 GAAGATCCTT TGATCTTTTC TACGGGGTCT GACGCTCAGT GGAACGAAAA CTCACGTTAA GGGATTTTGG
5421 TCATGAGATT ATCAAAAAGG ATCTTCACCT AGATCCTTTT AAATTAAAAA TGAAGTTTTA AATCAATCTA
5491 AAGTATATAT GAGTAAACTT GGTCTGACAG TTACCAATGC TTAATCAGTG AGGCACCTAT CTCAGCGATC
5561 TGTCTATTTC GTTCATCCAT AGTTGCCTGA CTCCCCGTCG TGTAGATAAC TACGATACGG GAGGGCTTAC
5631 CATCTGGCCC CAGTGCTGCA ATGATACCGC GAGACCCACG CTCACCGGCT CCAGATTTAT CAGCAATAAA
5701 CCAGCCAGCC GGAAGGGCCG AGCGCAGAAG TGGTCCTGCA ACTTTATCCG CCTCCATCCA GTCTATTAAT
5771 TGTTGCCGGG AAGCTAGAGT AAGTAGTTCG CCAGTTAATA GTTTGCGCAA CGTTGTTGCC ATTGCTACAG
5841 GCATCGTGGT GTCACGCTCG TCGTTTGGTA TGGCTTCATT CAGCTCCGGT TCCCAACGAT CAAGGCGAGT
5911 TACATGATCC CCCATGTTGT GCAAAAAAGC GGTTAGCTCC TTCGGTCCTC CGATCGTTGT CAGAAGTAAG
5981 TTGGCCGCAG TGTTATCACT CATGGTTATG GCAGCACTGC ATAATTCTCT TACTGTCATG CCATCCGTAA
6051 GATGCTTTTC TGTGACTGGT GAGTACTCAA CCAAGTCATT CTGAGAATAG TGTATGCGGC GACCGAGTTG
6121 CTCTTGCCCG GCGTCAATAC GGGATAATAC CGCGCCACAT AGCAGAACTT TAAAAGTGCT CATCATTGGA
6191 AAACGTTCTT CGGGGCGAAA ACTCTCAAGG ATCTTACCGC TGTTGAGATC CAGTTCGATG TAACCCACTC
6261 GTGCACCCAA CTGATCTTCA GCATCTTTTA CTTTCACCAG CGTTTCTGGG TGAGCAAAAA CAGGAAGGCA
6331 AAATGCCGCA AAAAAGGGAA TAAGGGCGAC ACGGAAATGT TGAATACTCA TACTCTTCCT TTTTCAATAT
6401 TATTGAAGCA TTTATCAGGG TTATTGTCTC ATGAGCGGAT ACATATTTGA ATGTATTTAG AAAAATAAAC
                                                                         NotI
6471 AAATAGGGGT TCCGCGCACA TTTCCCCGAA AAGTGCCACC TGACGTCTAA GAAACCGCGG CCGCAACAGA
6541 CGTCTAAGAA ACCATTATTA TCATGACATT AACCTATAAA AATAGGCGTA TCACGAGGCC CTTTCGTCTC
6611 GCGCGTTTCG GTGATGACGG TGAAAACCTC TGACACATGC AGCTCCCGGA GACGGTCACA GCTTGTCTGT
6681 AAGCGGATGC CGGGAGCAGA CAAGCCCGTC AGGGCGCGTC AGCGGGTGTT GGCGGGTGTC GGGGCTGGCT
6751 TAACTATGCG GCATCAGAGC AGATTGTACT GAGAGTGCAC CATATGCGGT GTGAAATACC GCACAGATGC
6821 GTAAGGAGAA AATACCGCAT CAGGCGCCAT TCGCCATTCA GGCTGCGCAA CTGTTGGGAA GGGCGATCGG
6891 TGCGGGCCTC TTCGCTATTA CGCCAGCTGG CGAAAGGGGG ATGTGCTGCA AGGCGATTAA GTTGGGTAAC
6961 GCCAGGGTTT TCCCAGTCAC GACGTTGTAA AACGACGGCC AGTGCC
```

METHODS AND MATERIALS FOR EXPRESSION OF A RECOMBINANT PROTEIN

This invention pertains to methods of producing a recombinant protein and recombinant expression vectors and host cells for use therein. This application is a continuation of U.S. application Ser. No. 11/295,006, filed Dec. 5, 2005, now abandoned, which claims the benefit of U.S. Provisional Application No. 60/633,056, filed Dec. 3, 2004, the disclosures of which are herein incorporated by reference in their entirety.

BACKGROUND OF THE INVENTION

Field of the Invention

Large-scale transient expression of recombinant proteins has been an area of rapid development in the past several years as an alternative or precursor to stable cell line development to generate multi-milligram quantities of protein (Wurm et al., *Curr. Opn. Biotech.* 10: 156-159 (1999)). Human embryonic kidney (HEK293) cells are one of the most widely used cell lines for transient expression and have been successfully adapted to suspension-growth to help facilitate culture scale-up. Recent reports have successfully demonstrated the usage of transiently expressing suspension-adapted HEK293 cells in 1-3 L cultures to generate recombinant proteins including soluble polypeptides, transmembrane proteins, and human antibodies (Durocher et al., *Nucleic Acids Res.* 30:1-9 (2002); Meissner et al., *Biotechnol. Bioeng.* 75: 197-203 (2000); and Cote et al., *Biotechnol. Bioeng.* 59: 567-575 (1998)).

In particular, Durocher et al. has shown that HEK293E cells expressing the Epstein-Barr virus (EBV) nuclear antigen-1 protein (EBNA1) were able to routinely generate >10 mg/L of a number of different recombinant proteins using the cationic polymer transfection reagent, polyethyleneimine (PEI) (Boussif et al., *Proc. Natl. Acad. Sci.* 92: 7297-7301 (1995); and Mislick et al., *Proc. Natl. Acad. Sci.* 93: 12349-12354 (1996)).

Despite these advances, there is still a need in the art for improved expression systems including optimized transient transfection systems for time- and cost-efficient production of recombinant proteins. The invention provides such optimized methods of producing recombinant proteins. These and other advantages of the invention, as well as additional inventive features, will be apparent from the description of the invention provided herein.

BRIEF SUMMARY OF THE INVENTION

The invention provides recombinant expression vectors useful in methods of producing a recombinant protein. One of the inventive recombinant expression vectors comprises a 3' untranslated region (UTR) of a light chain gene. Another recombinant expression vector provided herein comprises a 3'UTR and an Epstein-Barr virus origin of replication. Host cells comprising any of the inventive recombinant expression vectors are also provided herein.

The invention further provides methods of producing a recombinant protein. In a first method, the recombinant protein is a heterodimeric or heteromultimeric protein, either of which comprises a first polypeptide chain and a second polypeptide chain, wherein the first polypeptide chain is different from the second polypeptide chain. The method comprises contacting cells in a medium with a first vector and a second vector, wherein the first vector encodes the first polypeptide chain and the second vector encodes the second polypeptide chain, and the second vector is present in the medium in an amount which is about 1.5 to about 2.5 times as much as the amount of the first vector.

In a second method of producing a recombinant protein, the method comprises culturing cells, which have been contacted with a recombinant transient expression vector encoding the protein, in a medium in a membrane-enhanced culturing vessel, whereupon a recombinant protein is produced. Alternatively, the second method comprises culturing cells, which have been contacted with a recombinant transient expression vector encoding the protein, in a medium in a Fernbach flask.

In a third method, the recombinant protein is produced upon contacting cells with at least one of the inventive recombinant expression vectors described herein. In a fourth method, the recombinant protein is produced upon culturing host cells comprising any of the inventive recombinant expression vectors described herein.

BRIEF DESCRIPTION OF THE DRAWINGS

FIG. 1B is an illustration of the pMXT vector encoding a human $\gamma_2$ heavy chain, while

In FIG. 2A, cells were transfected with 1 μg/ml DNA and 1 μg/ml PEI. In FIG. 2B, cells were transfected with 2 μg/ml DNA and 2 μg/ml PEI. In FIG. 2C, cells were transfected with 5 μg/ml DNA and 5 μg/ml PEI. In FIG. 2D, cells were transfected with 1 μg/ml DNA and 2 μg/ml PEI. In FIG. 2E, cells were transfected with 2 μg/ml DNA and 4 μg/ml PEI. In FIG. 2F, cells were transfected with 5 μg/ml DNA and 10 μg/ml PEI. In FIG. 2G, cells were transfected with 1 μg/ml DNA and 5 μg/ml PEI. In FIG. 2H, cells were transfected with 2 μg/ml DNA and 10 μg/ml PEI. In FIG. 2I, cells were transfected with 5 μg/ml DNA and 25 μg/ml PEI.

FIG. 10 shows SEQ ID NO: 1, which is the nucleotide sequence of pMXT5 (FIG. 1A) without any coding sequences. Restriction enzyme sites are labeled with the name of the enzyme above the position of the site. CMV promoter comprises nucleotides 1-1037; 5'UTR intron comprises nucleotides 888-974; MCS comprises nucleotides 1038-1061; LC 3' UT comprises nucleotides 1062-2560; OriP comprises nucleotides 2561-4550; pUC19 ori comprises nucleotides 4551-5220; and Ap comprises nucleotides 5221-6380.

DETAILED DESCRIPTION OF THE INVENTION

The invention provides recombinant expression vectors useful in methods of producing a recombinant protein. One of the inventive recombinant expression vectors comprises a 3' untranslated region (UTR) of a light chain gene. Another recombinant expression vector provided herein comprises a 3'UTR and an Epstein-Barr virus origin of replication (oriP). Inventive recombinant expression vectors optionally comprise a pUC19 origin of replication (pUC19ori).

For purposes herein, the term "recombinant expression vector" means a genetically-modified oligonucleotide (i.e., polynucleotide) construct that permits the production of a protein within a cell, when the construct comprises a nucleotide sequence encoding the protein, and the construct is contacted with the cell under conditions sufficient to have the protein expressed within the cell. As the expression vector is recombinant, the vector of the invention is not naturally-occurring as a whole. However, parts of the vectors can be naturally-occurring.

The recombinant expression vector can comprise any type of nucleotides, including, but not limited to DNA and RNA, which can be single-stranded or double-stranded, which can be synthesized or obtained in part from natural sources, and which can contain natural or non-natural or altered nucleotides. Examples of non-natural or altered nucleotides that can be used to generate the recombinant expression vectors include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, (acp3) w, and 2,6-diaminopurine.

The recombinant expression vector can comprise naturally-occurring or non-naturally-occurring internucleotide linkages, or both types of linkages, such as phosphoroamidate linkages or phosphorothioate linkages, instead of the phosphodiester linkages found between the nucleotides of an unmodified oligonucleotide. Preferably, the non-naturally occurring or altered nucleotides or internucleotide linkages do not hinder in any way the transcription or replication of the vector.

Figure 1A:
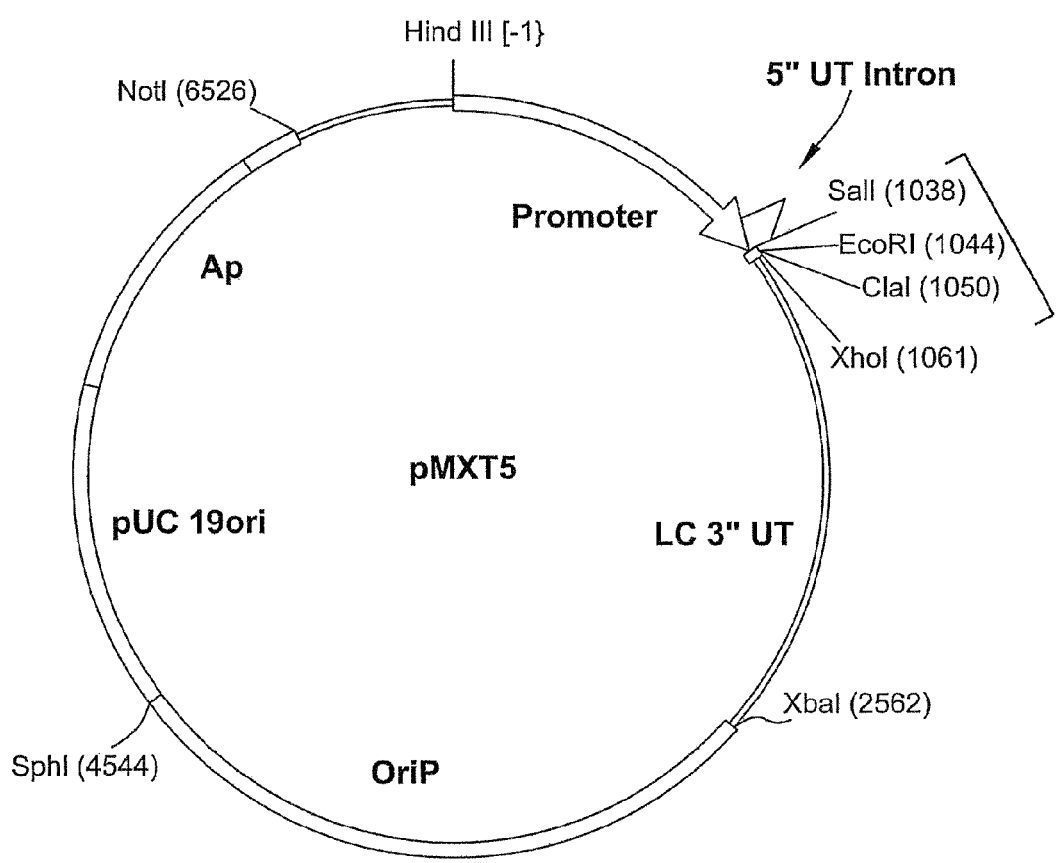
FIG. 1A is an illustration of the pMXT recombinant expression vector without any recombinant protein coding sequences.
Figure 1B:
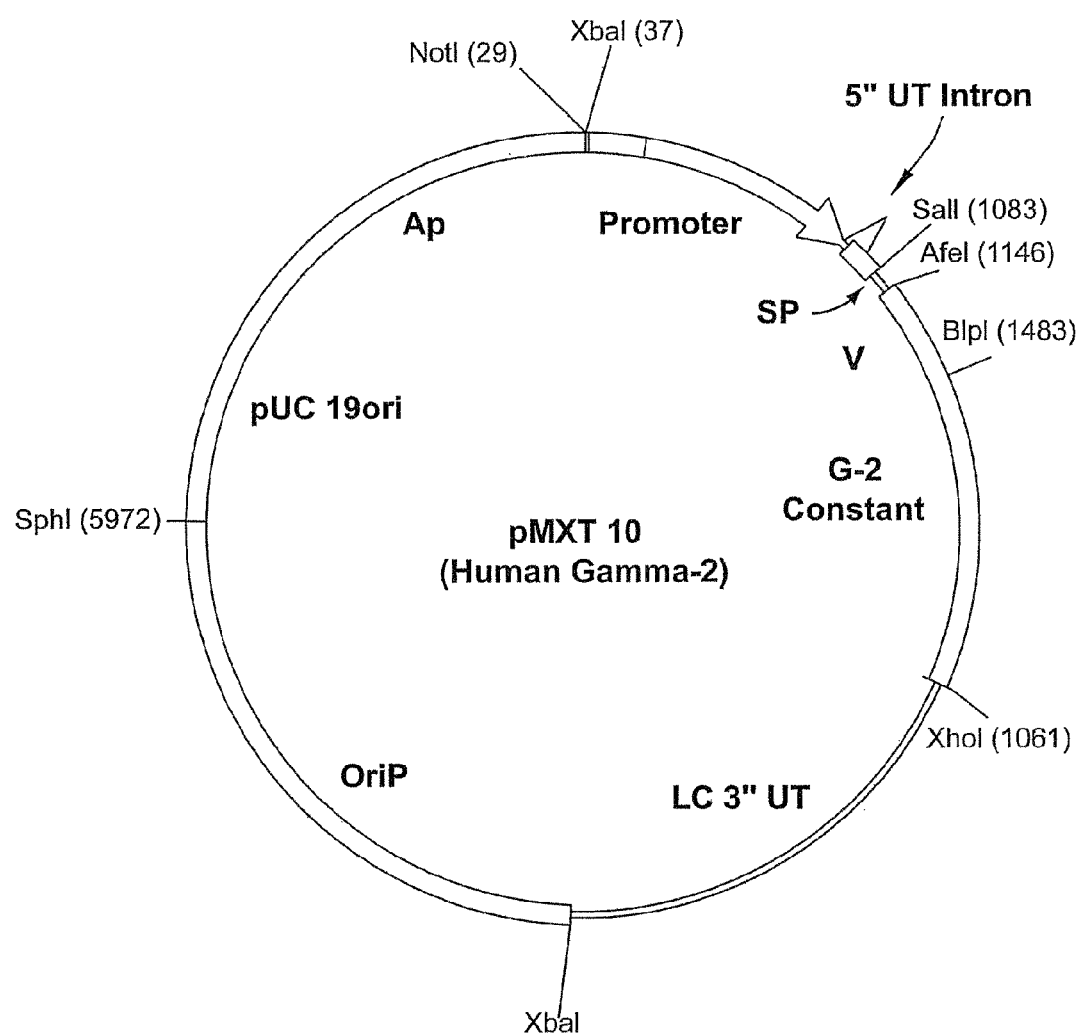
Figure 1C:
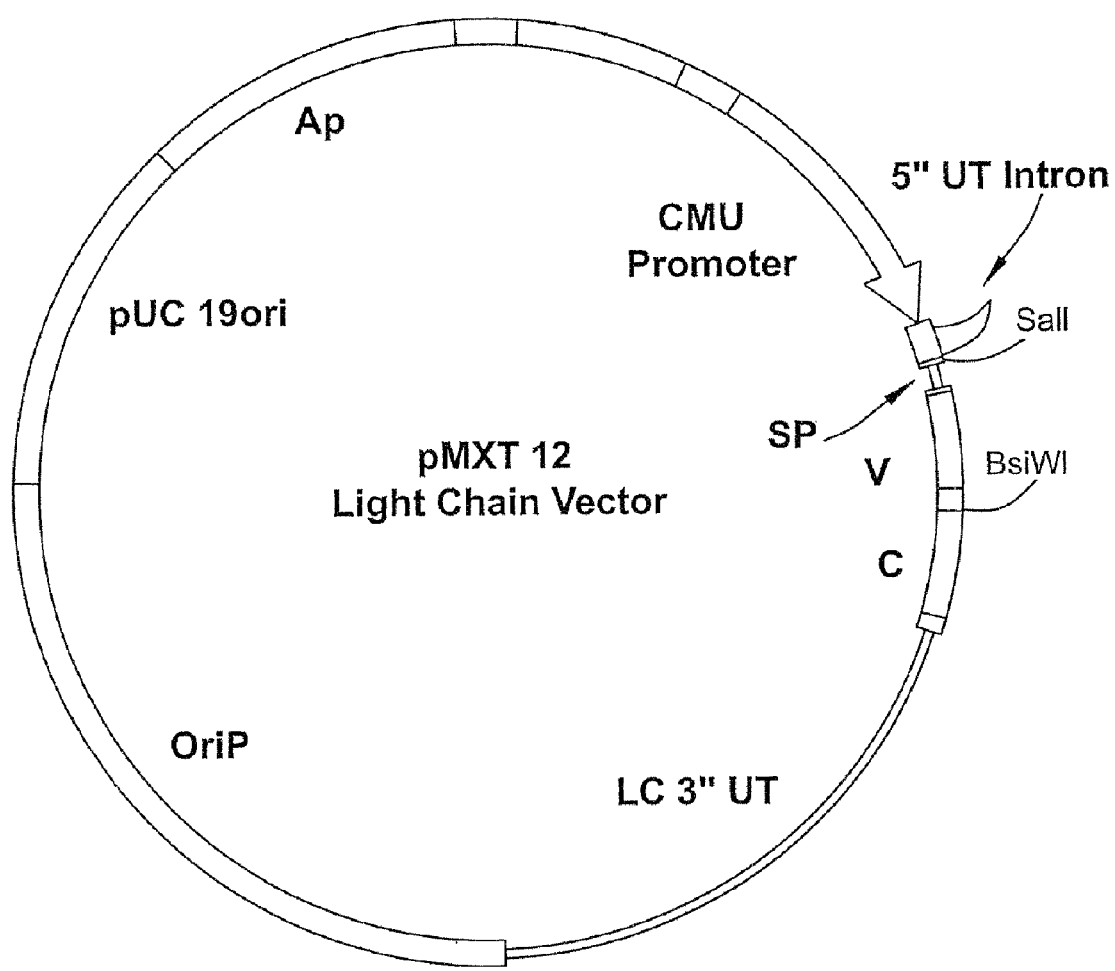
FIG. 1C is an illustration of the pMXT vector encoding a human κ light chain. The following abbreviations are used in FIGS. 1A-1C: Ap, ampicillin resistance marker; CMV promoter, cytomegalovirus promoter; MCS, multiple cloning sequence; 5' UT intron, 5' untranslated region intron; SP, signal peptide; V, variable region; C, constant region; LC 3' UT, light chain 3' untranslated region, OriP, Epstein-Barr virus origin of replication; pUC19ori, origin of replication from the pUC19 plasmid.

The recombinant expression vector can be any suitable recombinant expression vector, and can be used to transform or transfect any suitable host. For example, one of ordinary skill in the art appreciates that transformation or transfection is a process by which, for example, exogenous nucleic acids such as DNA are introduced into cells wherein the transformation or transfection process involves contacting the cells with the exogenous nucleic acids such as the recombinant expression vector as described herein. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121, and pBIN19 (Clontech). Examples of animal expression vectors include pEUK-C1, pMAM, and pMAMneo (Clontech). A preferred recombinant expression vector includes the pMXT vector as shown in FIGS. 1A-1C.

The recombinant expression vector can be prepared using standard recombinant DNA techniques described in, for example, Sambrook et al., *Molecular Cloning, a Laboratory Manual*, 2d edition, Cold Spring Harbor Press, Cold Spring Harbor, N.Y. (1989), and Ausubel et al., *Current Protocols in Molecular Biology*, Greene Publishing Associates and John Wiley & Sons, New York, N.Y. (1994).

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

A construct of a recombinant expression vector, which is circular or linear, can be prepared to contain a replication system functional in a prokaryotic or eukaryotic host cell. Replication systems can be derived from ColE1, 2μ plasmid, λ, SV40, bovine papilloma virus, and the like. The recombinant expression vector of the invention can comprise a replication system, which comprises an oriP. Preferably, the inventive recombinant expression vector comprises an oriP, and not an Epstein Barr virus nuclear antigen (EBVNA), which EBVNA is known to activate an oriP.

As used herein, the term "oriP" or "Epstein-Barr virus origin of replication" refers to a nucleotide sequence that is substantially identical to the Epstein-Barr virus origin of replication, which has the nucleotide sequence of nucleotides 2561-4550 of SEQ ID NO: 1. It is preferred that no insertions, deletions, inversion, and/or substitutions are present in this nucleotide sequence. However, one of ordinary skill in the art appreciates that the nucleotide sequence of nucleotides 2561-4550 of SEQ ID NO: 1 can have insertions, deletions, inversion, and/or substitutions that will not negatively affect the function of the nucleotide sequence, which is to promote high copy episomal plasmid replication. One of ordinary skill in the art further appreciates that such high copy episomal plasmid replication occurs in mammalian cells.

The recombinant expression vector also preferably comprises a pUC19 origin of replication. As used herein, the term "pUC19 origin of replication" refers to the nucleotide sequence of the origin of replication from a pUC19 vector, which is commercially available from Fermentas Life Sciences and has the nucleotide sequence of nucleotides 4551-5220 of SEQ ID NO: 1. It is preferred that no insertions, deletions, inversion, and/or substitutions are present in this nucleotide sequence. However, one of ordinary skill in the art appreciates that nucleotides 4551-5220 of SEQ ID NO: 1 can have insertions, deletions, inversion, and/or substitutions that will not affect the function of the nucleotide sequence, which is to promote high copy episomal plasmid replication. One of ordinary skill in the art further appreciates that such high copy episomal plasmid replication occurs in bacterial cells.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive recombinant expression vectors include, for instance, neomycin/G418 resistance genes, hygromycin resistance genes, histidinol resistance genes, tetracycline resistance genes, and ampicillin resistance genes.

The recombinant expression vector can comprise a native or normative promoter operably linked to the nucleic acid encoding the protein. The selection of promoters, e.g., strong, weak, inducible, tissue-specific, and developmental-specific, is within the ordinary skill in the art. Similarly, the combining of a nucleic acid with a promoter is also within the skill in the art. The promoter can be a viral promoter or a non-viral promoter. Preferably, the promoter is a viral promoter. More preferably, the viral promoter is a strong viral promoter, such as a cytomegalovirus (CMV) promoter. The CMV promoter is known in the art and has the nucleotide sequence of nucleotides 1-1037 of SEQ ID NO: 1. It is preferred that no insertions, deletions, inversion, and/or substitutions are present in this nucleotide sequence. However, one of ordinary skill in the art appreciates that nucleotides 1-1037 of SEQ ID NO: 1 can have insertions, deletions, inversion, and/or substitutions that will not affect the function of the nucleotide sequence, which is to drive the transcription of the recombinant protein coding sequence.

The recombinant expression vector comprises a 3'UTR of a light chain gene. Preferably, the recombinant expression vector comprises a 3'UTR of a light chain gene in combination with an Epstein-Barr virus origin of replication (oriP). As used herein, the term "3'UTR" refers to a nucleotide sequence of a gene that is untranslated and is located 3' to the stop codon of the coding sequence of that gene. The phrase "light chain gene" refers to a gene encoding a light chain of an immunoglobulin. Thus, in regard to the invention, the 3' UTR of a light chain gene is a nucleotide sequence that is originally found in a light-chain gene and that is inserted into the inventive vector. The light chain gene can be a light chain gene of any mammal, such as a human, mouse, rat, goat, rabbit, horse, pig, etc. Preferably, the light chain gene is a mouse (murine) light chain gene. More preferably, the mouse light chain gene has the nucleotide sequence of nucleotides 1062-2560 of SEQ ID NO: 1. It is preferred that no insertions, deletions, inversion, and/or substitutions are present in this nucleotide sequence. However, one of ordinary skill in the art appreciates that nucleotides 1062-2560 of SEQ ID NO: 1 can have insertions, deletions, inversion, and/or substitutions that will not affect the function of the nucleotide sequence, which is to provide signals for polyadenylation. With respect to the inventive vectors, the 3'UTR of a light chain gene is preferably located immediately 3' to the stop codon of the coding sequence of the vector. If no coding sequence is present, then the 3'UTR of a light chain gene preferably is located 3' to the multiple cloning sequence and/or the CMV promoter. The recombinant expression vector can comprise a single copy of a 3'UTR or multiple copies of a 3'UTR. Preferably, the recombinant expression vector comprises a single copy of a 3'UTR.

The recombinant expression vector preferably comprises a 5'UTR intron. As used herein, the term "5'UTR intron" refers to a nucleotide sequence that is transcribed but is removed by RNA splicing and thus not retained in the final transcript. It further is not translated and, thus, is not expressed as part of the protein, polypeptide, or peptide encoded by the vector. The 5'UTR intron is preferably located after the promoter in the 5' untranslated region of the recombinant expression vector. The 5'UTR intron promotes enhanced expression. The 5'UTR intron can be from any naturally-occurring source or can be constructed from portions of different sources, e.g., constructed from splice donor and acceptor sequences from different sources. For example, the 5'UTR intron comprises a portion of a CMV intron and a portion of a SV40 16 S intron. Preferably, the splice donor for the 5'UTR intron is from the sequence downstream of the start of transcription from the viral promoter, and the splice acceptor is from the SV40 16 S intron and has the nucleotide sequence of nucleotides 888-974 of SEQ ID NO: 1. It is preferred that no insertions, deletions, inversion, and/or substitutions are present in this nucleotide sequence. However, one of ordinary skill in the art appreciates that nucleotides 888-974 of SEQ ID NO: 1 can have insertions, deletions, inversion, and/or substitutions that will not affect the function of the nucleotide sequence, which is to drive the transcription of the recombinant protein coding sequence.

In a preferred embodiment, the recombinant expression vector comprises a 3' UTR, an oriP, a pUC19 origin of replication, a viral promoter, and a 5' UTR intron. Preferably, the viral promoter is a CMV promoter and the 5' UTR intron comprises a portion of a CMV intron and a portion of a SV40 16 S intron, e.g., comprises nucleotides 888-974 of SEQ ID NO: 1. Most preferably, the recombinant expression vector is the vector plasmid pMXT5, which is shown pictorially in FIG. 1A (pMXT5), and which has the nucleotide sequence (without any coding sequences) of SEQ ID NO: 1 (FIG. 10). For example, as shown in FIG. 10, the CMV promoter comprises nucleotides 1-1037; 5' UTR intron comprises nucleotides 888-974; MCS comprises nucleotides 1038-1061; LC 3' UT comprises nucleotides 1062-2560; OriP comprises nucleotides 2561-4550; pUC19 ori comprises nucleotides 4551-5220; and Ap comprises nucleotides 5221-6380.

The recombinant expression vector can be designed for either transient expression or for stable expression. Preferably, the vector of the invention promotes transient expression, i.e., is a recombinant transient expression vector, such that the vector is one that does not integrate into the genome of a host cell. Without being bound to any particular theory, it is believed that the recombinant expression vector can be made to be a transient expression vector by incorporating into the vector an oriP, which promotes high copy episomal plasmid replication.

The recombinant expression vector can comprise a nucleic acid sequence encoding any protein, suck as a hormone, growth factor, antibody, receptor, structural protein, enzyme, etc. The protein can be, for example, a therapeutic protein, and can be naturally-occurring or non-naturally occurring e.g., a genetically engineered protein including, for example, a fusion protein, a chimeric protein, etc. Preferably, the recombinant expression vector comprises such a nucleic acid for the expression of the protein. It is to be understood that the term "protein" as used herein includes parts or fragments thereof, and thus, polypeptides and peptides of any length are included within the meaning of this term. For example, polypeptides and peptides are included wherein the polypeptides can comprise, for instance, about 50 or more amino acids and the peptides can comprise, for instance, about 8-49 amino acids. The nucleic acid sequence encoding the protein can be obtained from any source, e.g., isolated from nature, synthetically generated, isolated from a genetically-engineered organism, and the like. An ordinarily skilled artisan will appreciate that any type of nucleic acid sequence (e.g., DNA, RNA, genomic DNA, and cDNA) that can be inserted into a recombinant expression vector can be used in connection with the invention. For example, the nucleic acid sequence encoding a protein can be naturally-occurring, e.g., a gene. Alternatively, the nucleic acid sequence encoding a protein can be non-naturally occurring, e.g., non-native to any organism, e.g., mammal. For instance, the nucleic acid sequence can be a codon optimized nucleic acid sequence in which codons within the nucleic acid sequence, which codons are not generally used by the host cell translation system, termed "rare codons," are changed by in vitro mutagenesis to preferred codons without changing the amino acids of the synthesized protein (Bradel-Tretheway et al., *J. Virol. Meth.*, 111: 145-156 (2003); Ramakrishna et al., *J. Virol.* 78: 9174-9189 (2004)). In addition, the nucleic acid sequence encoding a protein can be further modified, e.g., codon optimized, to improve the folding of the RNA, such that the folding of the RNA transcript encoded by the nucleic acid sequence is minimized. Whatever type of nucleic acid sequence is used, the nucleic acid sequence preferably encodes a secreted protein. By "secreted" is meant that the protein is released from the cell into the extracellular environment, thereby facilitating the purification of the protein. In this regard, the recombinant expression vector preferably comprises a signal sequence, which causes the expressed protein to be secreted from the cell by which it was expressed.

In a preferred embodiment, the recombinant expression vector comprises a nucleic acid encoding an immunogloblin chain, e.g., light chain or heavy chain. The immunoglobulin chain can be any immunoglobulin chain derived from any source, genetically-modified, or synthesized. Preferably, the immunoglobulin chain is a human immunoglobulin chain selected from the group consisting of a $\gamma_1$ heavy chain, a $\gamma_2$ heavy chain, a $\gamma_4$ heavy chain, a κ light chain, and a λ light chain. Exemplary heavy chain constant region sequences include: a $\gamma_1$ heavy chain constant region, which is encoded by the nucleotide sequence of SEQ ID NO: 4 and comprises the amino acid sequence of SEQ ID NO: 5; a $\gamma_2$ heavy chain constant region, which is encoded by the nucleotide sequence of SEQ ID NO: 6 and comprises the amino acid sequence of SEQ ID NO: 7; and a $\gamma_4$ heavy chain constant region, which is encoded by the nucleotide sequence of SEQ ID NO: 8 and comprises the amino acid sequence of SEQ ID NO: 9. Exemplary light chain constant region sequences include: a κ light chain constant region, which is encoded by the nucleotide sequence of SEQ ID NO: 10 and comprises the amino acid sequence of SEQ ID NO: 11, and a λ light chain constant region, which is encoded by the nucleotide sequence of SEQ ID NO: 12 and comprises the amino acid sequence of SEQ ID NO: 13. Exemplary antibody heavy and light chains include: an LDP-01 heavy chain, which is encoded by the nucleotide sequence of SEQ ID NO: 14 and comprises the amino acid sequence of SEQ ID NO: 15, and an LDP-01 light chain, which is encoded by the nucleotide sequence of SEQ ID NO: 16 and comprises the amino acid sequence of SEQ ID NO: 17. The LDP-01 antibody is referred to herein as Ab#1 and has been described in WO 2004/033693 (PCT/US2003/010154) and U.S. Patent Application Publication No. 2003/0203447 A1.

In this regard, the recombinant expression vector desirably comprises an antibody signal sequence, which promotes the secretion of the antibody into the extracellular environment. Suitable antibody signal sequences are known in the art. For example, a preferred signal sequence comprises SEQ ID NO: 2 or SEQ ID NO: 3.

The recombinant expression vector can alternatively comprise a nucleic acid sequence encoding a functional fragment of a protein. The term "functional fragment" which is synonymous with "functional part" or "functional portion," when used in reference to a protein, refers to any part or fragment of the protein, which part or fragment retains a biological activity of the protein of which it is a part. Functional fragments encompass, for example, those parts of a protein (the parent protein) that retain a function of the parent protein to a similar extent, the same extent, or to a higher extent, as the parent protein. For instance, if the protein is an immunoglobulin, functional fragments thereof can include any portion of the immunoglobulin which, for example, retains the ability to bind to the antigen of the parent immunoglobulin. Also, for example, if the protein is a cell surface receptor, functional fragments thereof can include any portion of the cell surface receptor which, for instance, retains the ability to bind to the ligand of the parent cell surface receptor. In reference to the parent protein, the functional fragment can comprise, for instance, about 10%, 25%, 30%, 50%, 60%, 80%, 90%, 95%, or more of the parent protein. The functional portion can comprise additional amino acids at the amino or carboxy terminus of the portion, or at both termini, which additional amino acids are not found in the amino acid sequence of the parent protein. Desirably, the additional amino acids do not interfere with the biological function of the functional portion.

The invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The cell can be a cultured cell or a primary call, i.e., isolated directly from an organism, e.g., a human. The cell can be an adherent cell or a suspended cell, i.e., a cell that grows in suspension. Suitable host cells are known in the art and include, for instance, DH5α *E. coli* cells, Chinese hamster ovarian (CHO) cells, monkey VERO cells, COS cells, HEK293 cells, and the like. For purposes of amplifying or replicating the recombinant expression vector, the host cell is preferably a prokaryotic cell. More preferably, the host cell is a DH5α cell. For purposes of producing a recombinant protein, the host cell is preferably a mammalian cell. Most preferably, the host cell is a human cell. While the cell can be any cell of the human body, it is preferred that the cell is a human embryonic kidney cell. More preferred is that the human embryonic kidney cell expresses an Epstein Barr virus nuclear antigen-1 (EBNA-1) protein, e.g., a 293E cell.

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The invention further provides methods of producing a recombinant protein. In a first method, the recombinant protein is a heterodimeric or heteromultimeric protein comprising a first polypeptide chain and a second polypeptide chain, wherein the first polypeptide chain is different from the second polypeptide chain. The first method comprises contacting cells in a medium with a first vector and a second vector, wherein the first vector encodes the first polypeptide chain and the second vector encodes the second polypeptide chain, and the second vector is present in the medium in an amount which is about 1.5 to about 2.5 times as much as the amount of the first vector, whereupon a recombinant protein is produced. The first and second vectors can be any suitable vector and preferably are inventive recombinant expression vectors as described herein.

For purposes of the first inventive method of producing a protein, the first and second vectors can independently be any type of vector, i.e., the first and second vectors can have the same regulatory elements but differ only in the recombinant protein coding sequence contained therein. By way of example, both the first vector and second vector can be the pMXT vector as shown in FIG. 1A. Preferably, each of the first vector and the second vector is one of the inventive recombinant expression vectors described herein. Most preferably, the first and second vectors are pMXT vectors. For example, it is preferred that each of the first and the second vector is a recombinant transient expression vector. It is also preferred that each of the first and second vector comprises a 3'UTR of a light chain gene and an oriP. It is also preferred that each of the first and second vector comprises a viral promoter, a pUC19 origin of replication, a 5'UTR intron, or a combination of any of the foregoing. Preferably, the viral promoter is a CMV promoter, and the 5'UTR intron comprises nucleotides 888-974 of SEQ ID NO: 1. Moreover, it is preferred that each of the first and second vector comprises an antibody signal sequence.

Also, with respect to the first inventive method of producing a protein, the second vector is present in the medium in an amount which is about 1.5 to about 2.5, e.g., 1.6, 1.7, 1.75, 1.8, 1.9, 2.0, 2.125, 2.25, 2.3, 2.4, and 2.5, times as much as the amount of the first vector. Preferably, the second vector is present in the medium in an amount which is about 1.75 to about 2.25 times as much as the amount of the first vector. More preferably, the second vector is present in the medium in an amount which is about twice as much as the amount of the first vector.

The invention further provides a second method of producing a recombinant protein. The second method comprises culturing cells, which have been contacted with a recombinant transient expression vector encoding the protein, in a medium in a membrane-enhanced culturing vessel, whereupon a recombinant protein is produced. The second method can alternatively comprise culturing cells, which have been contacted with a recombinant transient expression vector encoding the recombinant protein, in a medium in a Fernbach flask, whereupon a recombinant protein is produced. The recombinant transient expression vector can be any suitable such vector and preferably is an inventive recombinant expression vector as described herein.

In a third method, the recombinant protein is produced upon contacting cells with at least one of the inventive recombinant expression vectors described herein. In a fourth method, the recombinant protein is produced upon culturing any of the inventive host cells comprising any of the inventive recombinant expression vectors described herein.

Any suitable method can be employed to contact cells with a first vector, a second vector, or a recombinant expression vector, such that the cells express the protein encoded by the vector. Methods of contacting cells, such that the cells are modified to express a particular protein, polypeptide, or peptide, are well-known in the art. See the references listed in Sambrook et al. (1989), supra. Suitable methods of contacting cells to this end include, for instance, infection with a viral vector, transfection with a lipofection reagent, cationic polymer, DEAE, or calcium phosphate, and electroporation.

The cells can be contacted with a first vector, a second vector, or a recombinant expression vector in the presence of a suitable cationic polymer. Suitable cationic polymers for transfecting cells are known in the art, and include, for example, polylysine and polyethyleneimine (PEI). In a preferred embodiment of the inventive method, the cationic polymer is PEI. PEI can be linear or branched and can vary in molecular weight, depending on the number of base units, which comprise the polymer. Preferably, the PEI is a linear PEI. More preferably, the linear PEI has a molecular weight of about 25 kDa. Although the amount of PEI used in the method can be any amount, it is preferred that the linear PEI is present in an amount that is about 1.5 to about 4.5, e.g., 1.5, 1.6, 1.75, 2.0, 2.25, 2.5, 2.6, 2.7, 2.75, 2.8, 2.9, 3.0, 3.2, 3.3, 3.4, 3.5, 3.6, 3.7, 3.75, 3.8, 3.9, 4.0, 4.1, 4.25, 4.3, 4.4, and 4.5, times the amount of the vector(s) contacting the cells. Preferably, the PEI is present in an amount that is about 2.5 to 3.5 times the amount of the vector(s) contacting the cells. More preferably, the PEI is present in an amount that is about twice the amount of the vector(s) contacting the cells.

For purposes of the inventive method comprising contacting cells with more than one vector, e.g., a first vector and a second vector, the cells can be contacted with the first vector and second vector in a sequential fashion, e.g., first vector contacted with the cells before the second vector. Alternatively, the cells can be contacted with the first vector and second vector simultaneously. Preferably, the cells are contacted with the first vector and second vector simultaneously. For example, in a method comprising contacting cells with more than one vector, the cells can be contacted with a first vector before or simultaneously with a second or additional vector.

As used herein, the term "culturing" is synonymous with "maintaining." Methods of culturing cells are known in the art (see, e.g., *Tissue Engineering Methods and Protocols*, Morgan and Yarmush (eds.), Humana Press, Inc., Totowa, N.J., 1999). As one ordinarily skilled recognizes, the conditions under which cells are cultured varies depending on the cell type. The conditions include temperature of the environment, the culturing vessel containing the cells, the composition of the various gases, e.g., $CO_2$, which comprises the cell culture atmosphere or environment, the medium in which the cells are maintained, the components and pH of the medium, the density at which cells are maintained, the schedule by which the medium needs to be replaced with new medium, etc.

These parameters are often known in the art or can be empirically determined. For example, with respect to the inventive methods, wherein cells are cultured in a medium, e.g., a first medium, a second medium, etc., any method can be employed to culture the cells in the medium, such that the cells express (and, in some instances, secrete) the protein encoded by the vector, which was contacted to the cells.

The cells are desirably cultured in a membrane-enhanced culturing vessel or a Fernbach flask. For purposes herein, the term "membrane-enhanced culturing vessel" refers to a container for holding cell cultures that have been improved upon by the addition of at least one membrane. Suitable membrane-enhanced culturing vessels include membrane-based cell culture vessels, dialysis-based cell culture vessels, membrane-based high density cell culture vessels, and two-compartment vessels. The term "vessel" as used herein is synonymous with systems, reactors, bioreactors, flasks, and devices. Suitable membrane-enhanced culturing vessels include, for instance, MINIPERM flasks, OPTICELL flasks, and the CELLINE™ CL1000 (referred to herein as INTEGRA flasks or INTEGRA CL1000 flasks), which are commercially available from companies, such as IBS Integra Biosciences AG (Chur, Switzerland), OptiCell (Westerville, Ohio), VWR, Fisher Scientific, and Labmate (Asia). Most preferably, the membrane-enhanced culturing vessel is an INTEGRA CL1000. For example, one of the ordinary skill in the art appreciates that a membrane-enhanced culturing vessel such as an Integra flask may comprise a nutrient chamber and a cultivation chamber, wherein nutrients from a media reservoir in the nutrient chamber pass through a semi-permeable membrane into the cultivation chamber containing cells so as to provide a continuous supply of nutrients and wherein the membrane also allows for diffusion of metabolites out of the cultivation chamber and away from contact with the cells but does not permit diffusion of a recombinant protein produced by the cells (e.g., an antibody or antibody fragment) out of the cultivation chamber, and further wherein the cells also have sufficient gas exchange such as access to oxygen and carbon dioxide through a separate silicone membrane at the bottom of the vessel.

As used herein, the term "Fernbach flask" refers to a commercially available Corning® polycarbonate Erlenmeyer flask having the Fernbach design. Such flasks are commercially-available from companies such as Life Sciences.

Without being bound to any particular theory, membrane-enhanced flasks (e.g., INTEGRA CL1000, OPTICELL flasks, and MINIPERM flasks) and Fernbach flasks are particularly suitable for culturing transfected cells, for example, transiently transfected cells, as these devices permit efficient gas exchange between the cells and the environment, e.g., the incubator environment, which permits optimal cell growth and production of the recombinant protein. Under certain conditions, shake flasks can also be suitable culturing vessels in which cells can be cultured for optimal cell growth and production of the recombinant protein. It should be understood that any flask or culturing vessel that permits efficient gas exchange between the cells and the environment are included in the scope of the invention and are not limited to only the aforementioned flasks and culturing vessels.

In the inventive methods comprising culturing cells, the medium can be any suitable medium for culturing cells known in the art. The medium can be, for example, a culture medium containing 1% low immunoglobulin (Ig) fetal bovine serum (FBS). Alternatively, the medium can be a serum-free cell culture medium, e.g., IS293™ medium. In some instances, the medium is preferably a serum-free IS293™ medium (Irvine Scientific, Irvine, Calif.).

The cell cultures of the inventive methods can be initiated or seeded at any suitable cell density. As one of ordinary skill in the art recognizes, the seeding density depends on a variety of factors, such as cell type, culturing conditions, and the day which has been selected for harvesting or purifying the recombinant protein from the cell culture. Desirably, the cell density is within the range of about $1.0 \times 10^6$ to about $2.0 \times 10^7$ (e.g., about $1.0 \times 10^6$ to about $1.5 \times 10^7$). More preferably, the initiating seeding cell density of the cell culture is about $3.0 \times 10^6$ to about $1.0 \times 10^7$. Without being bound to any particular theory, it is believed that the seeding density of cells, which have been transiently transfected with a vector encoding a protein, is a factor in obtaining efficient production of a recombinant protein.

For purposes of the inventive methods, the cells that are cultured or are contacted with a first vector, a second vector, or a recombinant expression vector can be any cell, such as those described herein as "host cells." For example, the cells that are cultured and/or contacted with one or more than one recombinant expression vector can be any host cells. Preferably, the cells are mammalian cells, and, more preferably, the cells are human cells. The cells are desirably human embryonic kidney cells. In a most preferred embodiment, the human embryonic kidney cells express Epstein-Barr virus nuclear antigen-1 protein (EBNA-1), e.g., 293E cells.

Cells, which have been contacted with a recombinant transient expression vector, can be obtained by transiently transfecting cells by any method known in the art, including those described herein. Recombinant transient expression vectors are known in the art and include, for instance, pCEP4, pcDNA3, and any of the recombinant expression vectors described herein which comprise an oriP. Preferably, the recombinant transient expression vectors are pMXT vectors. For example, the vectors can be any of the inventive recombinant expression vectors as described herein.

With respect to the first method of producing a recombinant protein (e.g., comprising contacting cells with a first vector and a second vector), the method can further comprise the second inventive method of producing a recombinant protein. That is, the method of producing a recombinant protein can further comprise the step of culturing the cells, which have been contacted with a first vector and a second vector, in a second medium in a membrane-enhanced culturing vessel (e.g., an INTEGRA CL1000, an OPTICELL flask, a MINIPERM flask), a Fernbach flask, or like flask. In such an embodiment, the second medium can be different from the medium in which the first and second vectors are present. For purposes of the methods, which comprise culturing cells in a membrane-enhanced culturing vessel, a Fernbach flask, or like flask, the suitable medium for use in such a vessel or flask can be a serum-free cell culture medium, e.g., IS293 medium. Preferably, the medium is serum-free IS293 medium (Irvine Scientific, Irvine, Calif.).

With respect to the second inventive method of producing a recombinant protein, the method can comprise the first inventive method of producing a recombinant protein. One of ordinary skill in the art recognizes that the methods described herein can be combined in such a way, such that all of the limitations of the methods are met. Such a combined method is within the scope of the invention.

With respect to any of the inventive methods comprising culturing cells, e.g., in a membrane-enhanced culturing vessel, a Fernbach flask, or like flask, the method can further comprise purifying or isolating the recombinant protein from the medium, e.g., the serum-free medium. As used herein, the terms "purifying" and "isolating" do not necessarily refer to absolute purity or isolation, as one of ordinary skill in the art appreciates that a partially purified or partially isolated protein can be useful or of value.

Methods of purifying proteins from mixtures are known in the art. Suitable purification methods include, for example, chromatography, electrophoresis, and the like. Suitable chromatographic methods of purifying polypeptides include, for example, HPLC, ion-exchange chromatography, affinity chromatography, etc. Preferably, the purifying comprises chromatographing the medium through a resin, such as a cationic resin, an anionic resin, and an affinity resin. If the polypeptide is an immunoglobulin chain, the purifying preferably comprises the use of resin comprising *Staphylococcus aureus* Protein A, which is a bacterially-produced protein that binds to the Fc regions of IgG antibodies. More preferably, the purifying comprises centrifuging the medium through a column comprising Protein A, e.g., centrifuging the medium through a Protein A spin column (which is commercially available from Pro-Chem).

The purifying can occur at any point in time after culturing the cells, which have been contacted with a vector. In some instances, it is preferable for the purifying to occur after about 3 days of culturing, e.g., after about 3, 4, 5, 6 or more days. In other instances, it is preferable for the purifying to occur after about 7 days of culturing, e.g., after about 7, 8, 9, 10, 11, 12, 13, 14, 15 or more days.

The invention provides fast and efficient methods of producing high levels of recombinant proteins. In some instances, at least 300 μg/ml recombinant protein is produced after 3 days of culturing. In other instances, at least 500 μg/ml recombinant protein is produced after 3 days of culturing. In some preferred instances, at least 700 μg/ml recombinant protein is produced after 3 days of culturing.

The term "recombinant protein" as used herein, refers to any protein or part thereof that is produced by a genetically-engineered organism. For example, the recombinant protein can be any of the proteins described herein.

For purposes of the first method of producing a recombinant protein, the recombinant protein is a heterodimeric protein or a heteromultermeric protein, such as a tetramer, which comprises two copies of two different polypeptide chains. Such proteins are known in the art, and include, for instance, hemoglobin, immunoglobulins, T cell receptors, and B cell receptors, etc. In a preferred embodiment of the first inventive method, the recombinant protein is a heterotetrameric protein. Desirably, the heterotetrameric protein is an immunoglobulin. In this instance, it is preferred that the first vector encodes a heavy chain of an immunoglobulin, or a part thereof, and the second vector encodes a light chain of an immunoglobulin, or a part thereof. The heavy chain can be any heavy chain of any immunoglobulin, as described herein. The light chain can be any light chain of any immunoglobulin, as described herein. Exemplary antibody heavy and light chains: an LDP-01 heavy chain, which is encoded by the nucleotide sequence of SEQ ID NO: 14 and comprises the amino acid sequence of SEQ ID NO: 15, and an LDP-01 light chain, which is encoded by the nucleotide sequence of SEQ ID NO: 16 and comprises the amino acid sequence of SEQ ID NO: 17. The LDP-01 antibody is referred to herein as Ab#1 and has been described in WO 2004/033693 (PCT/US2003/010154) and U.S. Patent Application Publication No. 2003/0203447 A1.

EXAMPLES

The following examples further illustrate the invention but, of course, should not be construed as in any way limiting its scope.

Example 1

This example demonstrates the construction of recombinant expression vectors of the invention.

Transient expression vectors for expression of any gene were constructed with a multilinker site containing unique restriction sites positioned between the 3' end of the CMV promoter and the 5' end of the mouse light chain 3' untranslated region. Transient expression vectors containing cDNAs, which encode light chain κ or λ genes or heavy chain $\gamma_1$, $\gamma_2$, or $\gamma_4$ genes, under the control of a CMV promoter (Boshart et al., *Cell* 41: 521-530 (1985)) and mouse light chain 3' untranslated region (Xu et al., *J. Biol. Chem.* 261: 3838-3845 (1986)) were constructed. Unique restriction sites were positioned at the 5' end of the V region (e.g., SalI) and in the junction regions between the V and constant regions (BlpI for heavy chain, BsiWI for κ light chain and AvrII for lambda) for the cloning of any new V region adjacent to the desired cognate constant region. The vectors also contained the Epstein Barr virus oriP sequence (Reisman et al., *Mol. Cell. Biol.* 5: 1822-1832 (1985)) for episomal plasmid replication in 293E cells, the origin of replication from the vector pUC19, and the gene encoding resistance to ampicillin for selection of tranformants in *E. coli*. The transient expression vectors containing the multilinker sites, the heavy chain, and the light chain are shown in FIGS. 1A-1C.

Example 2

This example demonstrates a method of transiently transfecting cells for producing recombinant proteins.

293E cells (Invitrogen, R620-07) were maintained as adherent cultures in Dulbecco's Modified Eagle Medium (DMEM) (Gibco-Invitrogen) supplemented with 10% fetal bovine serum (FBS, Hyclone), 2 mM glutamine, and 250 μg/ml G418 antibiotic (Gibco-Invitrogen). For growth in suspension culture, the cells were adapted to the following serum-free media formulations: IS293™ (Irvine Scientific), IS293-V™ (Irvine Scientific), 293 SFM II (Gibco-Invitrogen), H-SFM (Gibco-Invitrogen), and HYQ®PF293 (HyClone). The cells were originally supplemented with 10% low IgG FBS (HyClone) and 2 mM glutamine and gradually weaned down to 1% low IgG FBS over a period of several weeks. Once in 1% low IgG FBS, the cells were transferred to shake flasks for continued adaptation to suspension growth. Growth and viability were monitored using the VICELL™ XR Cell Viability Analyzer (Beckman-Coulter).

All plasmids were transformed into DH5α cells (Invitrogen) and purified using endotoxin-free plasmid purification kits (QIAGEN®). For transfections in 6-well plates, 2 ml of cells at $5 \times 10^5$ cells/ml were seeded per well. For transfections in shake flask cultures, cells were seeded at $8 \times 10^5$ cells/ml at the appropriate volumes prior to transfection. DNA (2 μg/ml) was pre-incubated with linear polyethyleneimine (PEI, 25 kDa MW, Polysciences) at a concentration of 4 μg/ml for 10 min at room temperature prior to addition to cells. The DNA/

PEI mixture was then added to cells, and the cells with the DNA/PEI were either maintained in shake flasks or transferred to Integra flasks.

Example 3

This example demonstrates the determination of the optimal PEI:DNA ratio for transient transfections.

Adherent 293E cells grown in DMEM supplemented with 10% FBS in 6-well plates were transfected with pQBI-pGK (GFP expressing plasmid, Q-biogene) using linear polyethyleneimine (PEI) as described in Example 2. DNA (1 μg/ml, 2 μg/ml, or 5 μg/ml) was pre-incubated with linear PEI (1, 2, 4, 5, 10, or 25 μg/ml) for 10 min at room temperature prior to the addition to cells, then the PEI/DNA mixture was added to cells, and the cells were maintained in shake flasks or Integra flasks.

Figure 2A:
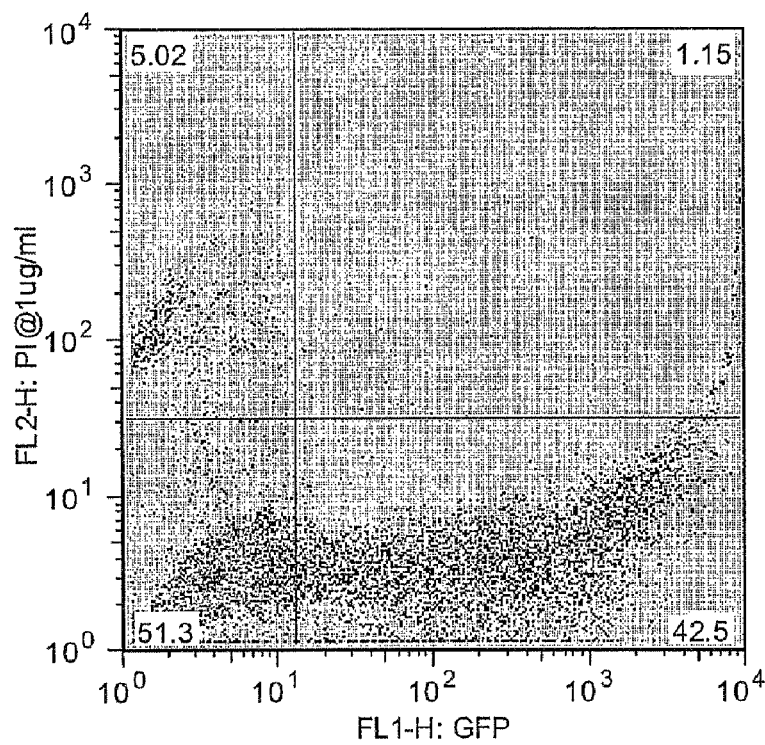
FIGS. 2A-2I are flow cytometry data graphs depicting the levels of fluorescence of green fluorescence protein (GFP) and propidium iodide (PI) under differing transfection conditions, specifically differing DNA and polyethyleneimine (PEI) concentrations.
Figure 2B:
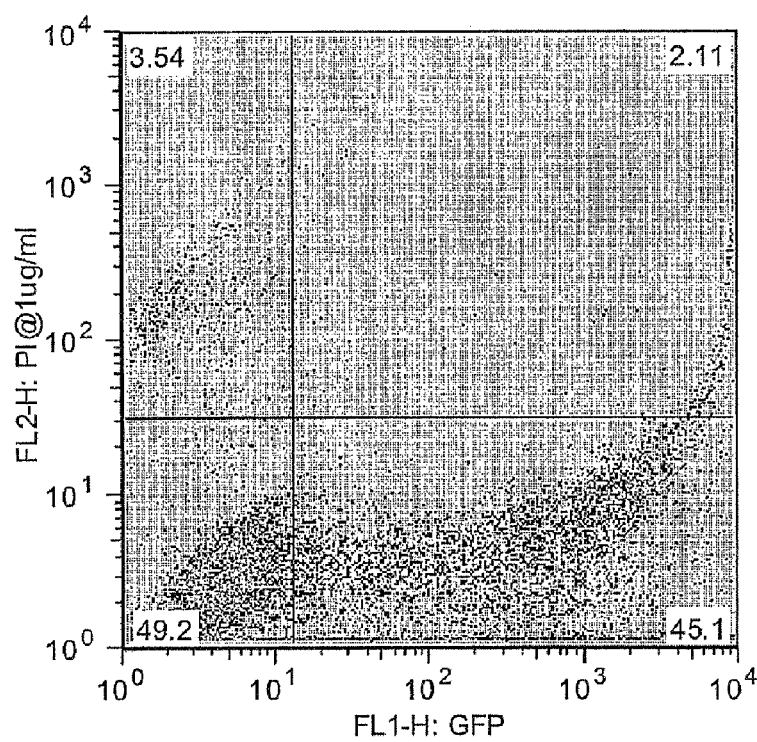
Figure 2C:
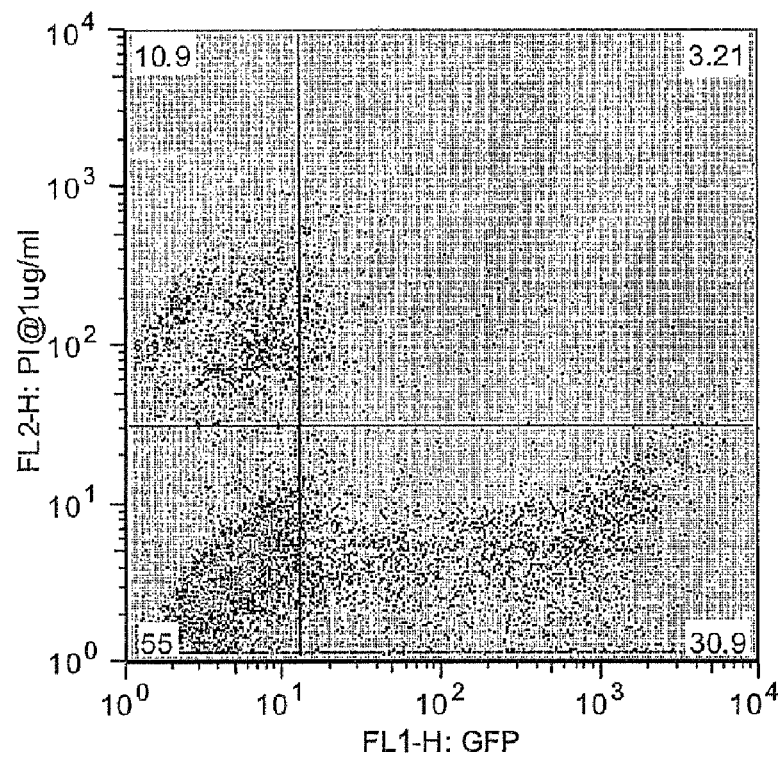
Figure 2D:
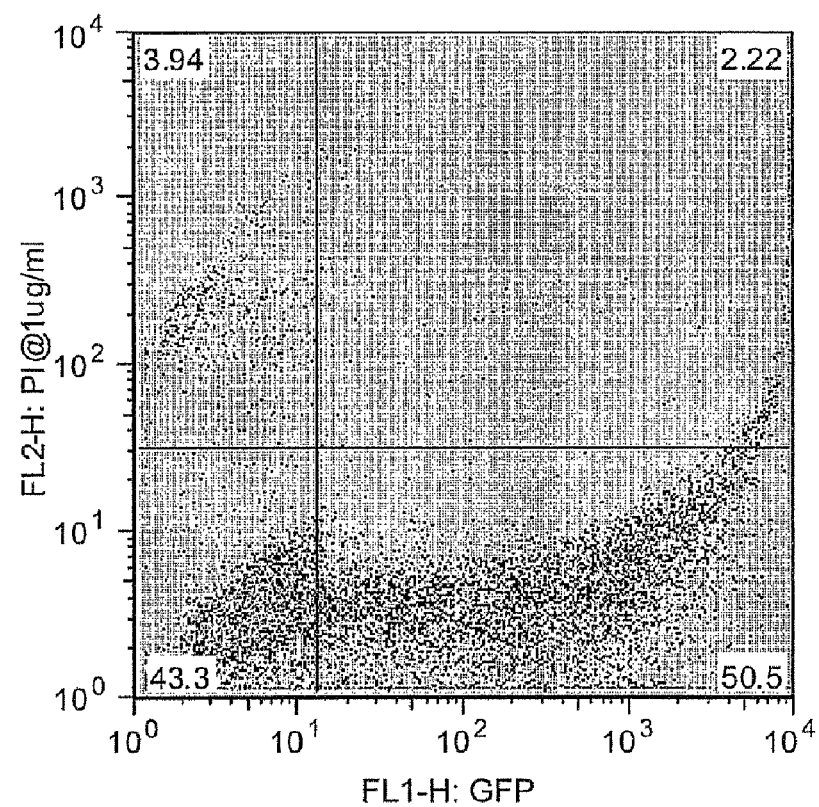
Figure 2E:
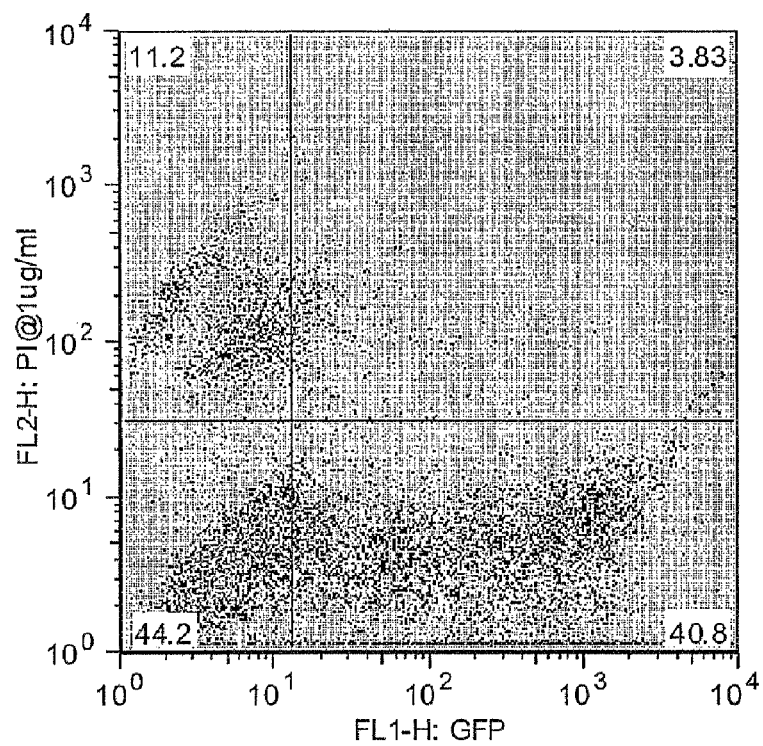
Figure 2F:
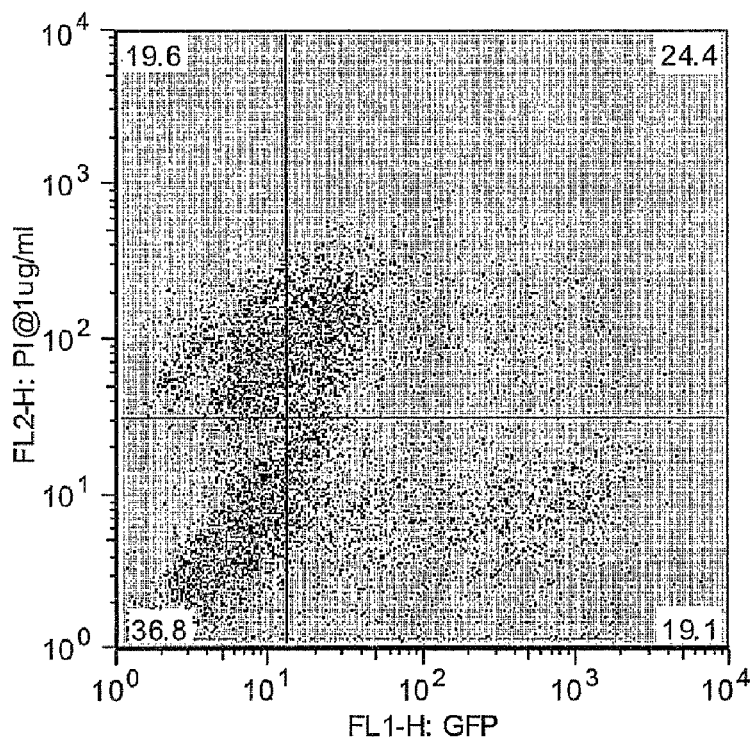
Figure 2G:
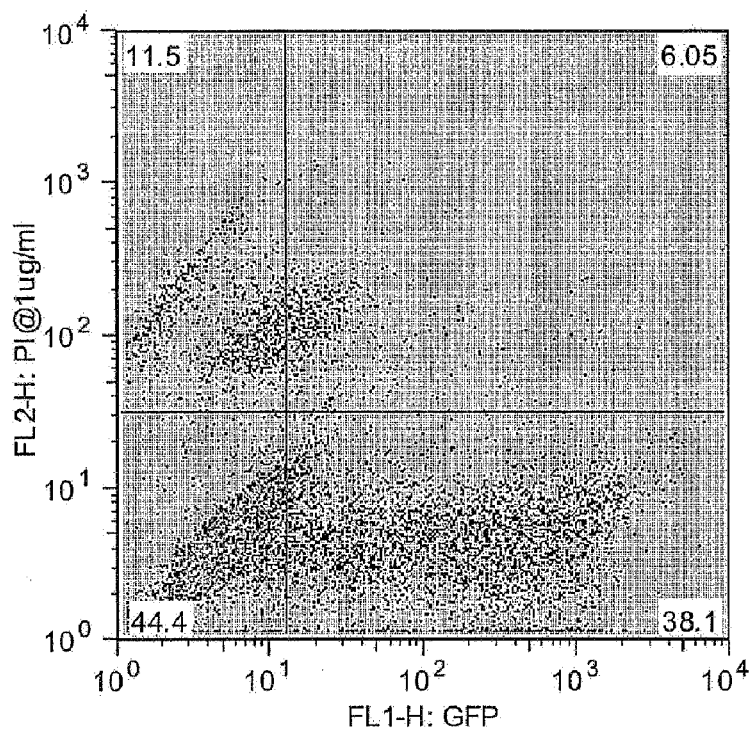
Figure 2H:
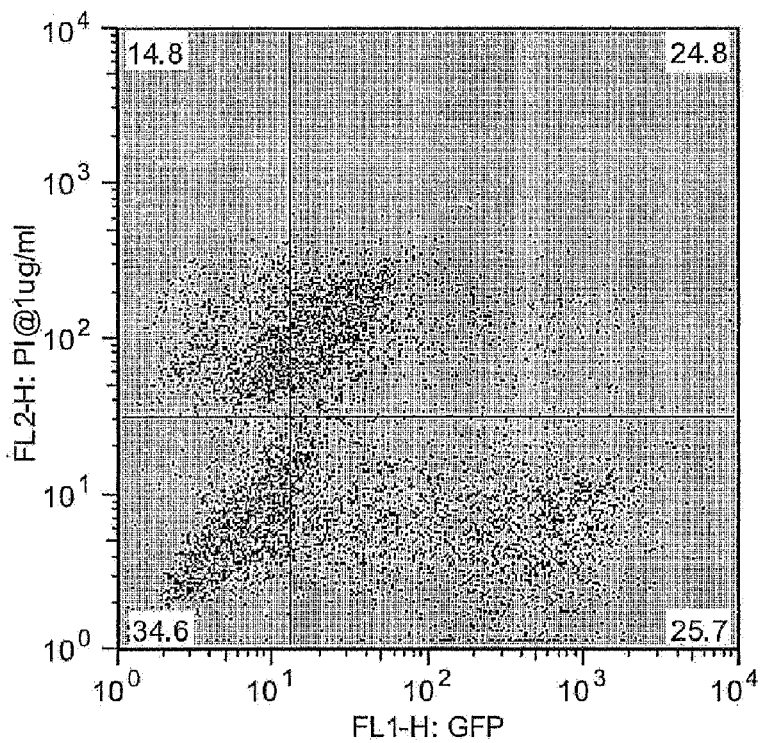
Figure 2I:
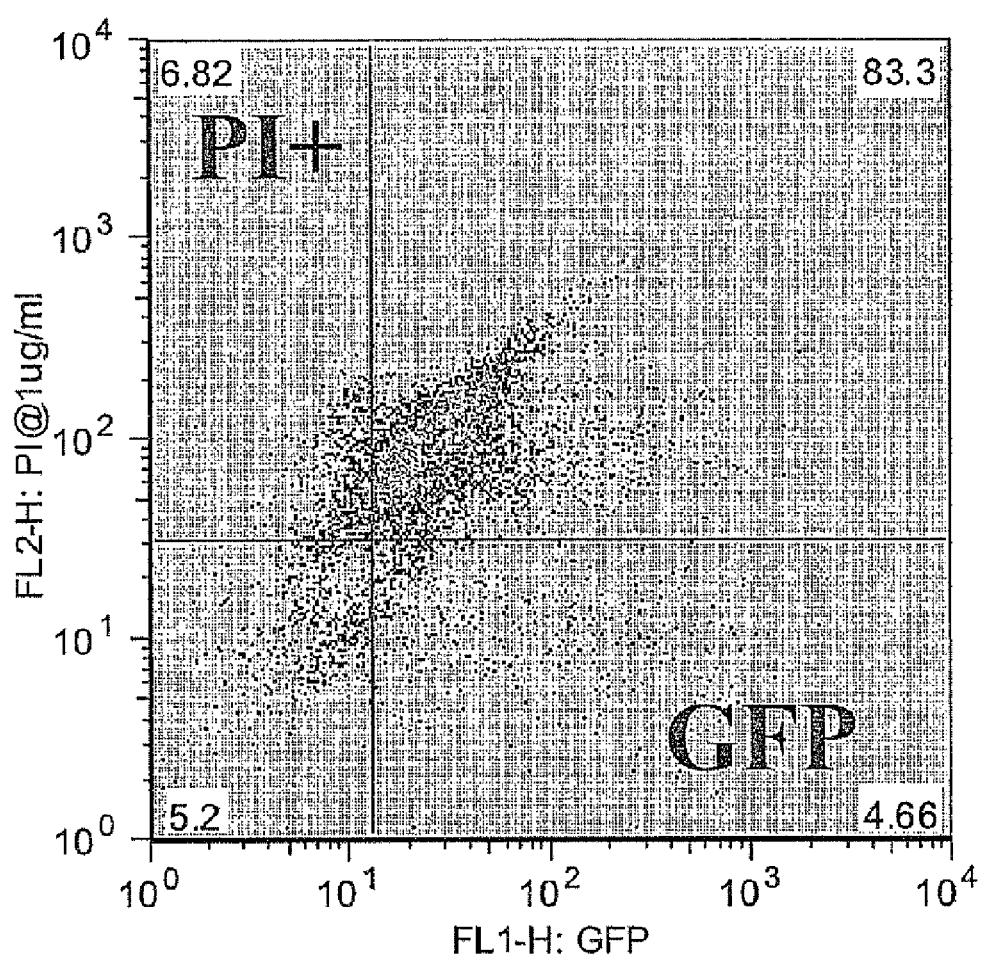

GFP expression was monitored 24 hours post-transfection using a Becton Dickinson FACSCAN® flow cytometer equipped with the Cytek Automated Microsampler System (AMS) 96-well plate reader. Flow data was analyzed using FLOWJO™ (Tree Star, Inc.). Cells also were counterstained with 1 μg/ml propidium iodide (PI) to determine cell viability. Growth and viability of the cells post-transfection were monitored using the VICELL™ XR Cell Viability Analyzer (Beckman-Coulter). The cells transfected with 1 μg/ml DNA and 1 μg/ml PEI (FIG. 2A); 2 μg/ml DNA and 2 μg/ml PEI (FIG. 2B); 5 μg/ml DNA and 5 μg/ml PEI (FIG. 2C); 1 μg/ml DNA and 2 μg/ml PEI (FIG. 2D); 2 μg/ml DNA and 4 μg/ml PEI (FIG. 2E); 5 μg/ml DNA and 10 μg/ml PEI (FIG. 2F); 1 μg/ml DNA and 5 μg/ml PEI (FIG. 2G); 2 μg/ml DNA and 10 μg/ml PEI (FIG. 2H); and 5 μg/ml DNA and 25 μg/ml PEI (FIG. 2I) were measured for GFP expression (x-axis) and PI staining (y-axis) by flow cytometry, and the resulting data was plotted in the series of graphs of FIGS. 2A-2I.

As shown in FIGS. 2A-2I, the DNA concentration of 1 μg/ml at a PEI:DNA ratio of 2:1 gave the highest percentage of cells expressing GFP with relatively low cellular cytotoxicity 24 hours post-transfection.

The results of this example demonstrated the production of recombinant protein and confirmed that the optimal PEI:DNA ratio for transient transfection is 2:1.

Example 4

This example demonstrates the determination of the optimal medium for culturing transiently transfected cells.

293E cells were grown and transfected in the presence of 1% low-IgG serum in 6-well plates and shake flasks, as described in Example 2. Twenty-four hours after transfection, 293E cells were adapted to suspension growth in one of 5 different serum-free media formulations (IS293™, H-SFM, IS293V™, SFMII, or HYQ®PF293) or one serum-containing media formulation (DMEM) as in Example 2.

Twenty-four to forty-eight hours later, GFP expression by transfected cells were determined as described in Example 3. Cells also were counterstained with 1 μg/ml PI to determine cell viability. Growth and viability of the cells post-transfection were monitored using the VICELL™ XR Cell Viability Analyzer (Beckman-Coulter). The resulting data from GFP expression (bars) and for PI staining (x) was plotted to form the graph of FIG. 3.

Figure 3:
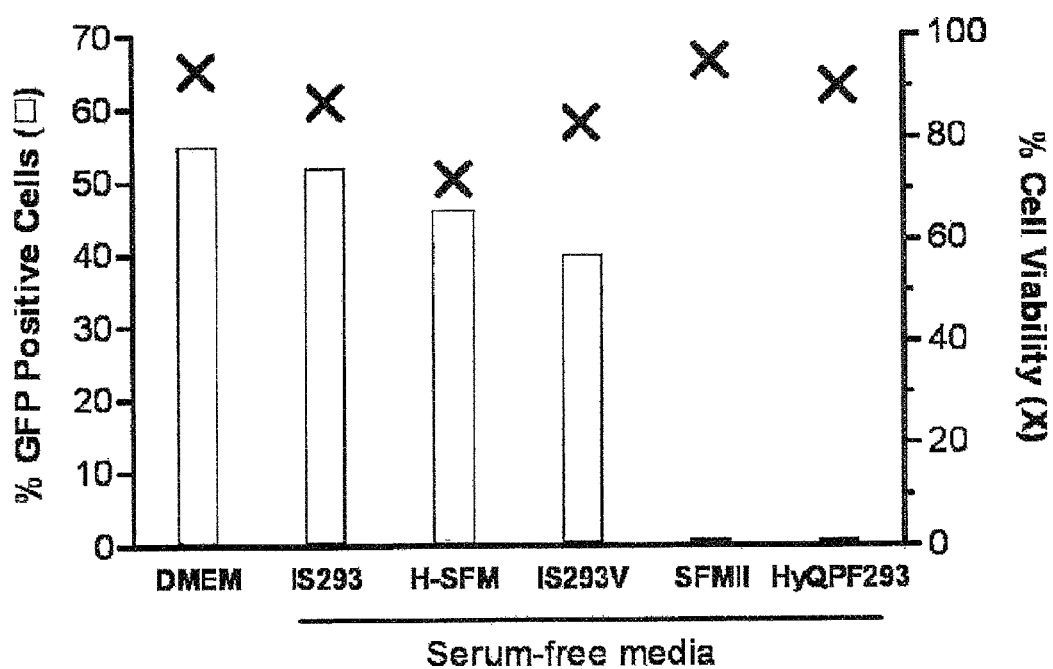
FIG. 3 is a graph showing the % cell viability (×) and % GFP positive 293E cells (■) that were adapted to suspension growth in different serum-free media and optimized for transfection. A control set of 293E cells were grown in DMEM.

As shown in FIG. 3, IS293™ medium (Irvine Scientific) gave the highest percentage of GFP-expressing cells with minimal cytotoxicity in shake flasks; values were comparable to those obtained with adherent 293E cells cultured in DMEM supplemented with 10% FBS.

The results of this example demonstrated that IS293™ medium is the optimal serum-free medium to be used with transiently transfected cells for producing recombinant proteins.

Example 5

This example demonstrates the determination of optimum heavy and light chain plasmid ratios for maximum antibody productivity.

Various ratios of pMXT (heavy chain (HC)):pMXT (light chain (LC)) (see Example 1) or pCEP4 (HC):pCEP4 (LC) were tested for effects on antibody productivity in cells grown in IS293™ medium supplemented with 1% low-IgG serum in shake flasks. The pCEP4 vector containing the nucleotide sequence encoding the Ab#1 heavy chain (SEQ ID NO: 14) was constructed by cloning the coding sequence into KpnI and Xho sites. The pCEP4 vector containing the nucleotide sequence encoding the Ab#1 light chain (SEQ ID NO: 16) was constructed by cloning the coding sequences into Nhe and Xho sites. The encoded heavy chain and light chain of Ab#1 is set forth as SEQ ID NOs: 15 and 17, respectively. All plasmids were amplified by transformation into DH5α cells and purified as described in Example 2. 293E cells were transiently transfected as described in Example 2. Transfected cells were transferred to IS293 medium in shake flasks for 7-10 days. Antibody expression by the cells transfected with a 1:1, 1:2, or 2:1 ratio of vector encoding HC:vector encoding LC, wherein the vectors were either pMXT or pCEP4 was determined by sandwich ELISA and the data analyzed in PRISM™ (GraphPad). The resulting data was plotted to form the graph of FIG. 4.

Figure 4:
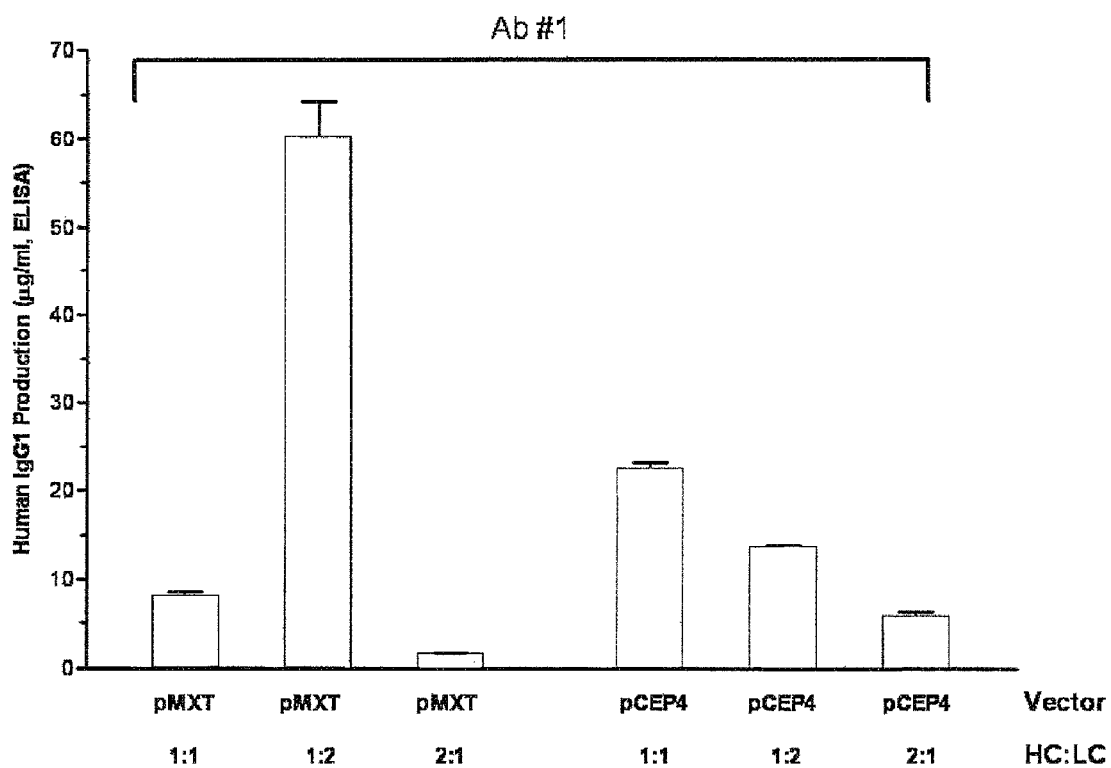
FIG. 4 is a graph showing the antibody production by cells which were co-transfected with different heavy chain (HC): light chain (LC) ratios of different vector types.

As shown in FIG. 4, a 1:2 ratio of HC:LC generated the highest antibody productivity with Ab#1 achieving levels of 60-70 μg/ml after 7-10 days. The highest productivity for Ab#1 (LDP-01) in pMXT was ~3× greater than the best output achieved using pCEP4.

The results of this example demonstrated that the pMXT vector is optimal for co-transfecting cells with vectors encoding different polypeptide chains at a ratio of 1:2.

Example 6

This example demonstrates that the level of antibody production by transiently transfected cells cultured post-transfection in membrane-enhanced culturing vessels are comparable to the level of antibody production achieved by transfected cells cultured post-transfection in shake flasks.

293E cells were transiently transfected in shake flasks as described in Example 2. Cells were either maintained in the shake flasks or transferred to 15 ml of medium and placed in INTEGRA CL1000 flasks. After 7-10 days, cell culture supernatant was harvested, clarified, and purified for antibodies using a standard Protein A column, if cells were cultured in shake flasks, or a Protein A spin column, if cells were cultured in INTEGRA flasks. Cell viability and antibody production of both sets of cells 0, 4, 7, and 14 days post-transfection were assayed as described in Examples 4 and 5, respectively. For antibody expression using the INTEGRA CL1000 flask, 200 ml of transfected 293E cells were resuspended in 15 ml of IS293™ medium supplemented with 1% low IgG FBS and 250 μg/ml G418 antibiotic and transferred into the membrane compartment. One liter of IS293™ medium was added to the upper media chamber.

Figure 5A:
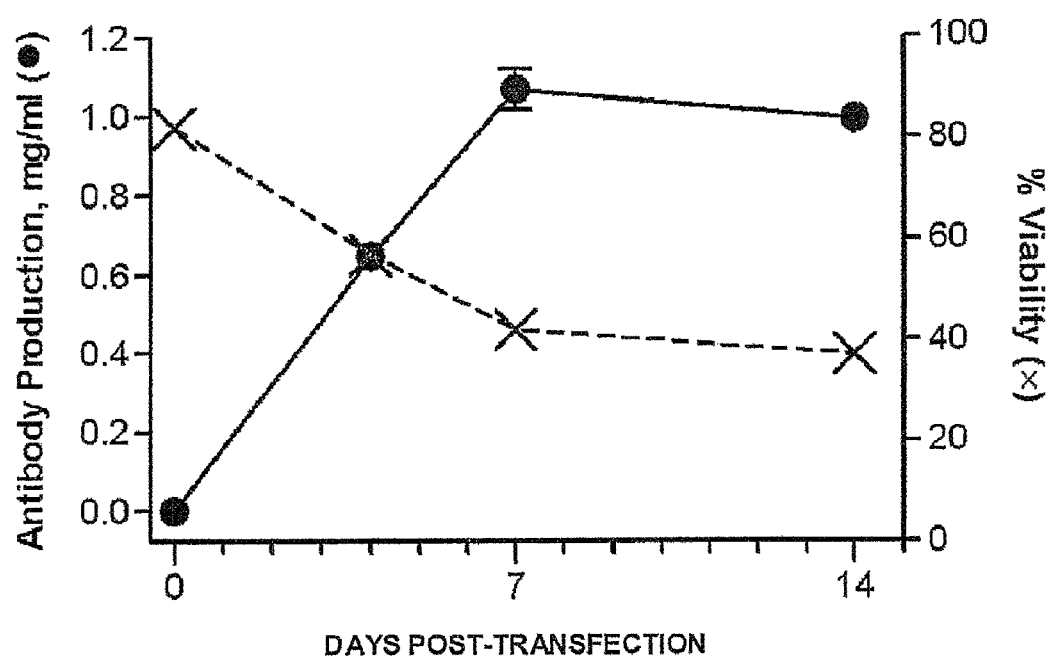
FIG. 5A is a graph showing antibody production (*) and cell viability (X) of transiently transfected 293E cells in INTEGRA flasks as a function of time post-transfection.
Figure 5B:
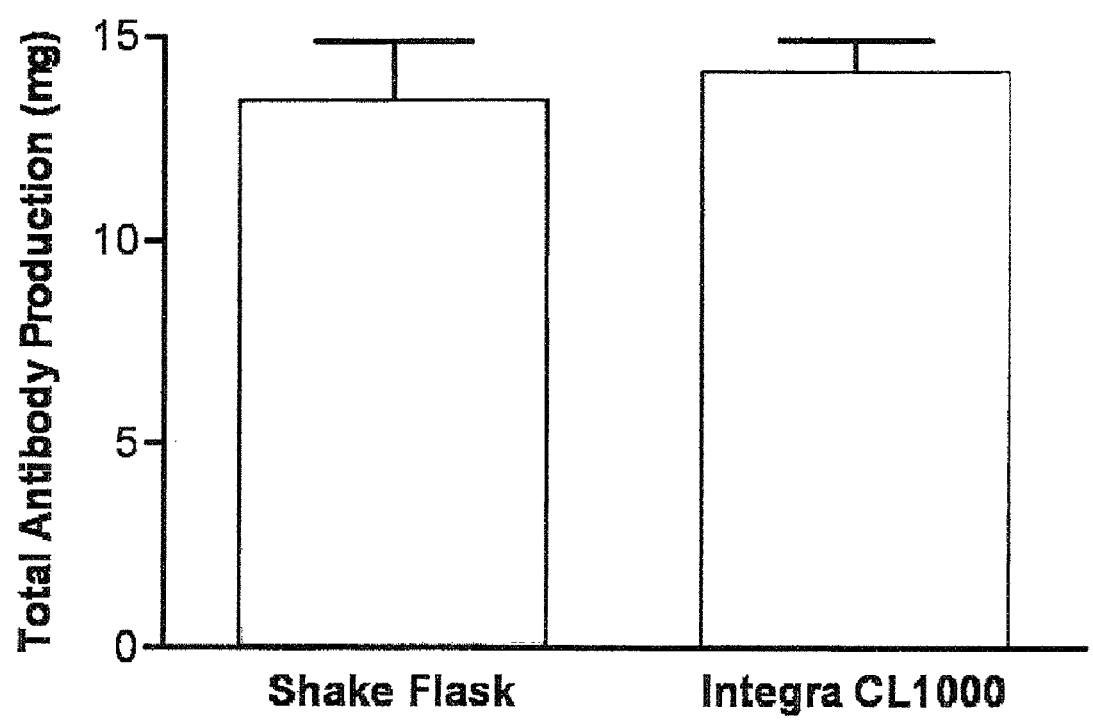
FIG. 5B is a graph showing the production of antibodies in shake flasks vs. INTEGRA flasks by transfected cell cultures at day 7 post-transfection.

The cell viability (x) and antibody production (*) of the transfected cells maintained in INTEGRA flasks are shown in FIG. 5A, whereas the levels of antibody production for Ab#1 by cells maintained in either shake flasks or by INTEGRA CL1000 flasks are shown in FIG. 5B.

As shown in FIG. 5A, antibody production of cells cultured in INTEGRA flasks peaked at 7 days, producing over 1 mg/ml antibody. This level is comparable to the level of antibody production of transiently transfected cells cultured in shake flasks as shown in FIG. 5B.

The results of this example demonstrated that INTEGRA flasks are suitable culturing vessels for maintaining small volumes of transiently transfected cells. The small volume permits the use of Protein A spin columns, which facilitates the purification of antibodies from the cell culture supernatant.

Example 7

This example demonstrates a method of producing antibodies in membrane-enhanced culturing vessels at optimized seeding densities.

Suspension-adapted HEK 293E cells were maintained in IS293™ medium (Irvine Scientific) supplemented with 1% low IgG FBS (HyClone), 2 mM glutamine (Gibco-Invitrogen), and 250 µg/ml G418 antibiotic (Gibco-Invitrogen). For transfection, cells were seeded at $8 \times 10^5$ cells/ml in shake flasks at the appropriate volumes prior to transfection. DNA encoding Ab#1 or Ab#2 (which differed from Ab#1) was pre-incubated with linear polyethyleneimine (PEI, 25 kDa MW, Polysciences) at optimized conditions (see, e.g., Example 3; see also, e.g., Handa et al., *American Society for Cell Biology*, poster presentation #1937 (2004)) prior to addition to cells. For antibody expression using the INTEGRA CL1000 flask, cells at the following seeding densities were resuspended in 30 ml of IS293™ medium supplemented with 1% low IgG FBS, 2 mM glutamine, and 250 µg/ml G418 antibiotic and transferred into the cultivation chamber: $1.3 \times 10^6$ (I-50), $2.7 \times 10^6$ (I-100), $5.3 \times 10^6$ (I-200), and $1.1 \times 10^7$ (I-400). For comparison, $8 \times 10^5$ cells (E-200) were seeded in Erlenmeyer flasks. All flasks were incubated for 3, 5, 7, or 10 days post-transfection. One ml samples from the nutrient chambers and cultivation chambers of the INTEGRA CL1000 flasks were removed and analyzed at 3, 5, 7, or 10 days post-transfection.

Figure 6A:
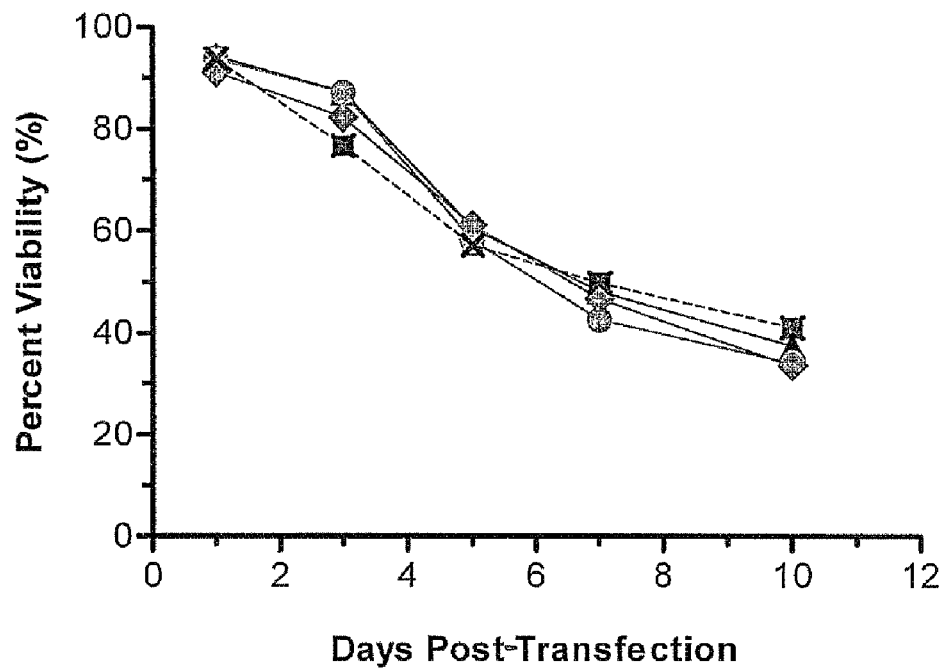
FIG. 6A is a graph of the percentage of viable cells transfected with DNA encoding Ab#1 as a function of time post-transfection.
Figure 6B:
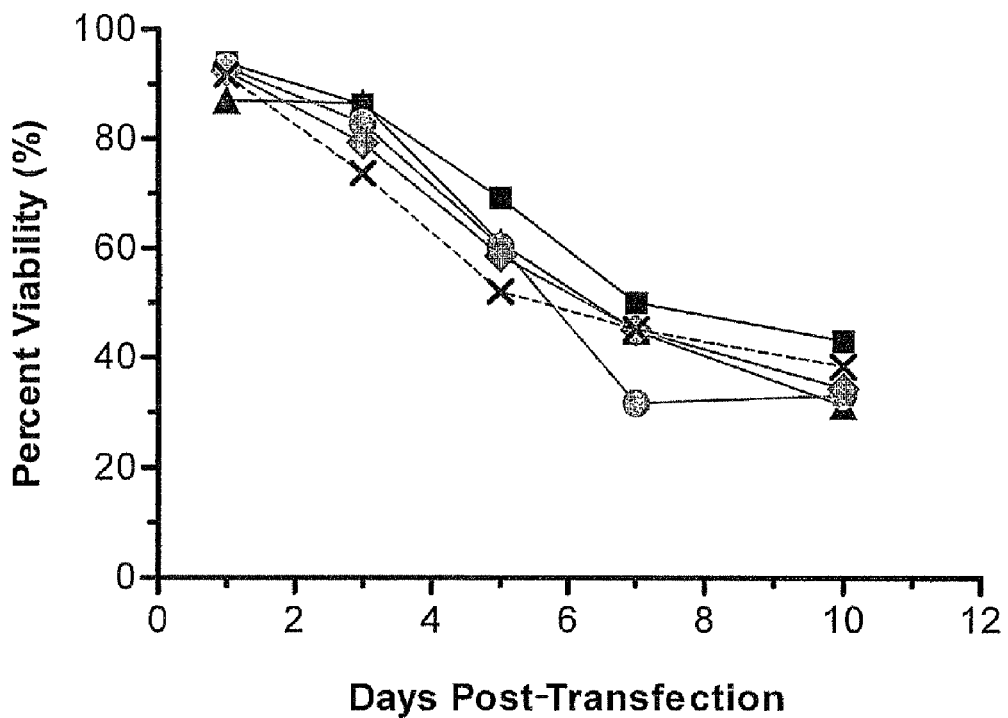
FIG. 6B is a graph of the percentage of viable cells transfected with DNA encoding Ab#2 as a function of time post-transfection. In both FIGS. 6A and 6B, ■ is I-50; ▲ is I-100; • is I-200; ♦ is I-400; and × is E-200.
Figure 7A:
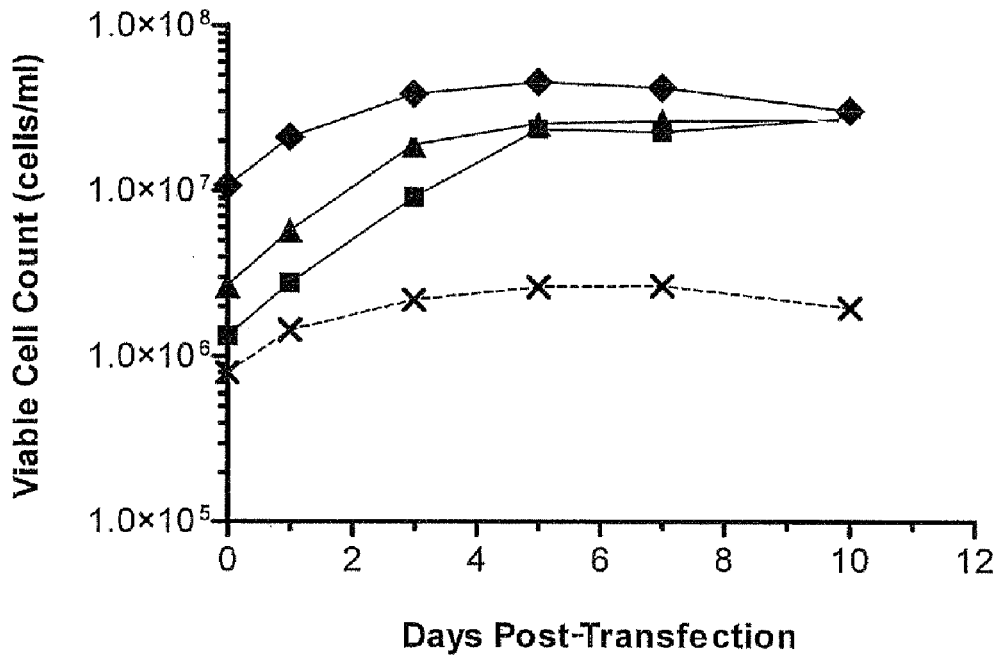
FIG. 7A is a graph of the number of viable cells transfected with DNA encoding Ab#1 as a function of time post-transfection.
Figure 7B:
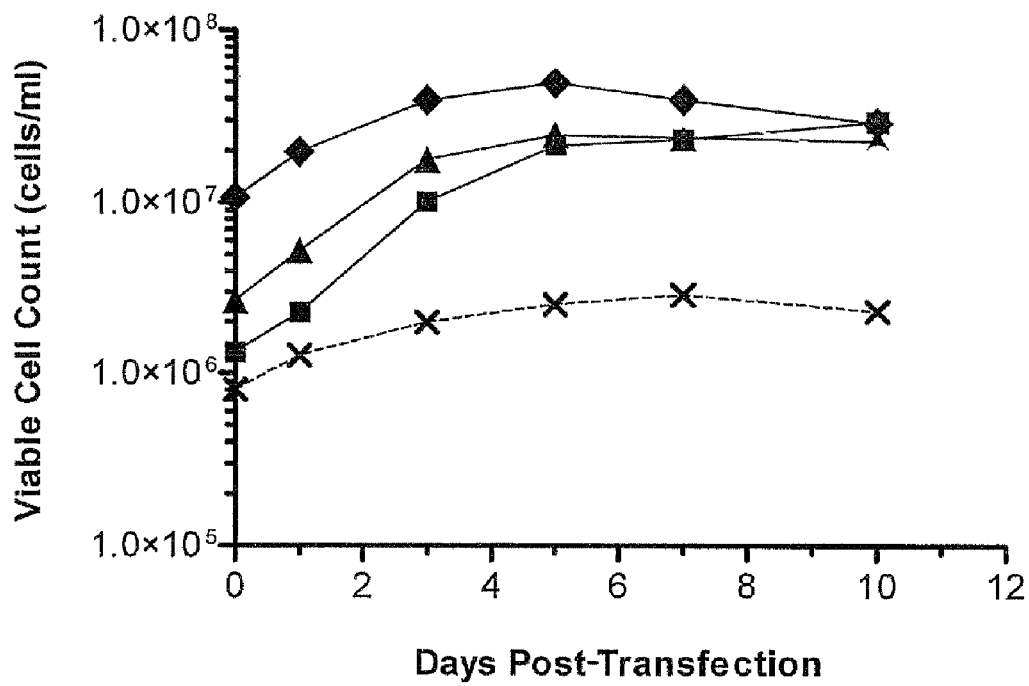
FIG. 7B is a graph of the number of viable cells transfected with DNA encoding Ab#2 as a function of time post-transfection. In both FIGS. 7A and 7B, ■ is I-50; ▲ is 1-100; • is I-200; ♦ is I-400; and × is E-200.

Growth and viability were monitored using the VICELL™ XR Cell Viability Analyzer (Beckman-Coulter). The percentage of viable cells 1, 3, 5, 7, and 10 days after transfection for cells transfected at different seeding densities is shown in FIGS. 6A and 6B. The viable cell count of cells 0, 1, 3, 5, 7, and 10 days after transfection for cells transfected at different seeding densities is shown in FIGS. 7A and 7B.

As shown in FIGS. 6A (Ab#1), 6B (Ab#2), 7A (Ab#1) and 7B (Ab#2), cell viability did not vary between flasks, but viable cell growth was improved in the Integra flasks for all seeding densities tested. Maximum densities of $3-5 \times 10^7$ cells/ml were achieved for all conditions over the 10 day analysis period.

Analytes, gases, and pH of the samples were determined 3, 5, 7, and 10 days post-transfection using a BIOPROFILE™ Chemistry Analyzer (Nova Biomedical). The data for selected nutrients and metabolites of the media containing cells producing Ab#1 or the media containing no cells (Media Only) are set forth in Table 1.

TABLE 1

| Nutrient | Sample | Flask Chamber | Media Only | Day 3 | Day 5 | Day 7 | Day 10 |
|---|---|---|---|---|---|---|---|
| Glucose (g/L) | I-50 | cultivation | 5.37 | 3.35 | 2.85 | 2.57 | 2.76 |
| | I-50 | nutrient | 5.36 | 5.11 | 4.49 | 4.12 | 3.47 |
| | I-100 | cultivation | 5.37 | 3.86 | 2.93 | 2.99 | 2.41 |
| | I-100 | nutrient | 5.36 | 5.05 | 4.39 | 3.97 | 3.85 |
| | I-200 | cultivation | 5.37 | 3.27 | 3.09 | 3.01 | 2.84 |
| | I-200 | nutrient | 5.36 | 4.62 | 4.12 | 3.68 | 3.10 |
| | I-400 | cultivation | 5.37 | 2.86 | 3.11 | 2.98 | 2.74 |
| | I-400 | nutrient | 5.36 | 4.52 | 3.94 | 3.67 | 3.23 |
| | E-200 | N/A | 5.36 | 4.42 | 2.51 | 2.36 | 2.06 |
| Glutamine (mmol/L) | I-50 | cultivation | 6.96 | 6.07 | 4.77 | 4.80 | 4.32 |
| | I-50 | nutrient | 6.82 | 6.30 | 5.89 | 5.54 | 4.79 |
| | I-100 | cultivation | 6.96 | 5.84 | 4.57 | 4.65 | 4.03 |
| | I-100 | nutrient | 6.82 | 6.37 | 5.88 | 5.41 | 5.10 |
| | I-200 | cultivation | 6.96 | 5.36 | 4.64 | 4.50 | 4.68 |
| | I-200 | nutrient | 6.82 | 6.07 | 5.62 | 5.19 | 4.63 |
| | I-400 | cultivation | 6.96 | 5.47 | 5.25 | 5.02 | 4.21 |
| | I-400 | nutrient | 6.82 | 6.37 | 5.91 | 5.68 | 5.12 |
| | E-200 | N/A | 6.82 | 6.31 | 5.82 | 5.53 | 5.08 |
| Lactate (g/L) | I-50 | cultivation | 0.26 | 1.92 | 2.42 | 3.17 | 2.82 |
| | I-50 | nutrient | 0.34 | 0.74 | 1.36 | 1.82 | 2.27 |
| | I-100 | cultivation | 0.26 | 1.85 | 2.43 | 2.74 | 2.82 |
| | I-100 | nutrient | 0.34 | 0.99 | 1.62 | 1.94 | 2.52 |
| | I-200 | cultivation | 0.26 | 2.47 | 2.32 | 2.84 | 2.72 |
| | I-200 | nutrient | 0.34 | 1.25 | 1.86 | 2.09 | 2.33 |
| | I-400 | cultivation | 0.26 | 2.57 | 2.31 | 2.78 | 2.66 |
| | I-400 | nutrient | 0.34 | 1.63 | 2.17 | 2.35 | 2.38 |
| | E-200 | N/A | 0.34 | 1.53 | 2.50 | 2.59 | 2.48 |

As shown by the resulting data, transiently transfected cells maintained in 30 ml media in the cultivation chamber of an Integra CL1000 flask can reach cell densities of up to $3-5 \times 10^7$ viable cells/ml (e.g., $4.5 \times 10^7$). Nutrients from the media reservoir in the nutrient chamber pass through a semi-permeable membrane into the cultivation chamber providing a continuous supply of essential nutrients. The membrane also allows for diffusion of metabolites out of the cultivation chamber and away from contact with cells. Cells also have efficient access to oxygen and carbon dioxide through a separate silicone membrane at the bottom of the flask.

The Integra supernatant from the cultivation chamber had higher glucose levels than shake flasks but lower glutamine levels. The levels of lactate appeared similar between the two cultures. The higher relative levels of glucose to lactate in the Integra cultures could indicate that the cells are generating more ATP by promoting efficient entry of pyruvate from glycolysis into the TCA cycle.

Antibody titers of transfected cells placed in Integra flasks or shake flasks at different seeding densities were determined using the EASY-TITER™ Human IgG Assay Kit (Pierce) 0, 3, 5, 7, and 10 days post-transfection. The data expressed as the concentration of antibody titers (µg/ml) is shown in FIGS. 8A (Ab#1) and 8B (Ab#2), whereas the data expressed as the total antibody yield (mg) is shown in Table 2.

TABLE 2

| | Day 3 | | Day 5 | | Day 7 | | Day 10 | |
|---|---|---|---|---|---|---|---|---|
| Sample | Yield (mg) | % of E-200 Max Yield | Yield (mg) | % of E-200 Max Yield | Yield (mg) | % of E-200 Max Yield | Yield (mg) | % of E-200 Max Yield |
| Ab#1 | | | | | | | | |
| E-200 | 7.6 | 52% | 14.5 | 100% | 7.4 | 51% | 7.6 | 52% |
| I-50 | 0.8 | 6% | 5.2 | 36% | 8.5 | 59% | 13.3 | 92% |
| I-100 | 5.2 | 36% | 8.3 | 57% | 14.7 | 101% | 24.0 | 166% |
| I-200 | 9.4 | 65% | 13.8 | 95% | 13.8 | 95% | 19.0 | 131% |
| I-400 | 11.00 | 76% | 15.7 | 108% | 14.3 | 99% | 11.7 | 81% |
| Ab#2 | | | | | | | | |
| E-200 | 4.1 | 50% | 6.3 | 77% | 7.5 | 92% | 8.2 | 100% |
| I-50 | 1.2 | 15% | 4.3 | 52% | 7.6 | 93% | 6.4 | 78% |
| I-100 | 3.5 | 43% | 8.3 | 101% | 10.4 | 127% | 12.9 | 157% |
| I-200 | 6.1 | 74% | 13.0 | 159% | 17.0 | 207% | 22.0 | 268% |
| I-400 | 10.8 | 132% | 17.8 | 217% | 21.0 | 256% | 22.0 | 268% |

Figure 8A:
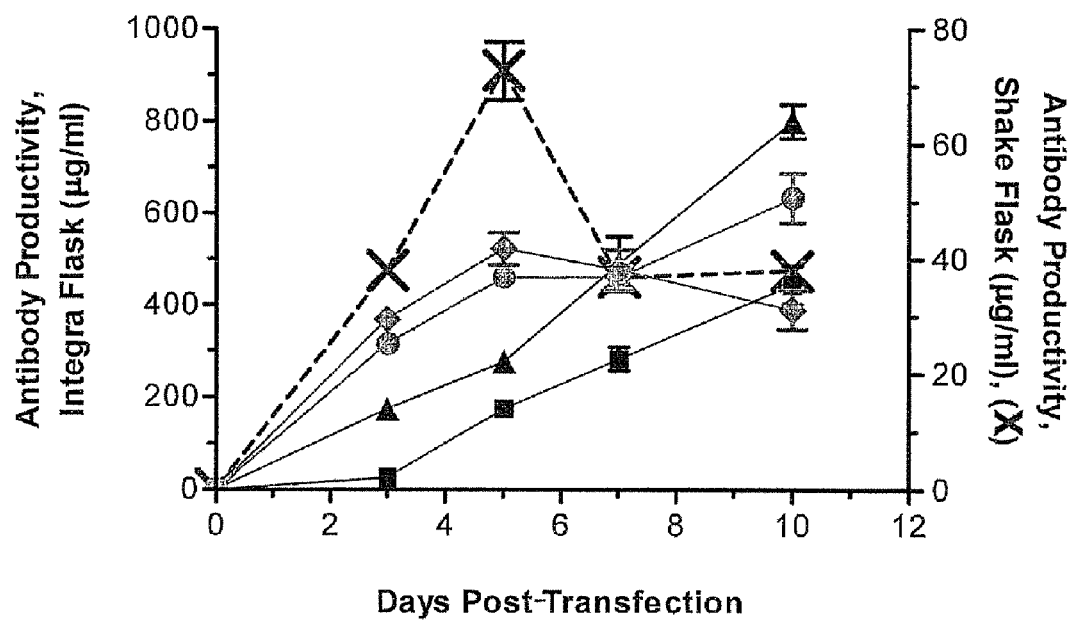
FIG. 8A is a graph of the concentration of antibody produced by cells transfected with DNA encoding Ab#1 as a function of time post transfection.
Figure 8B:
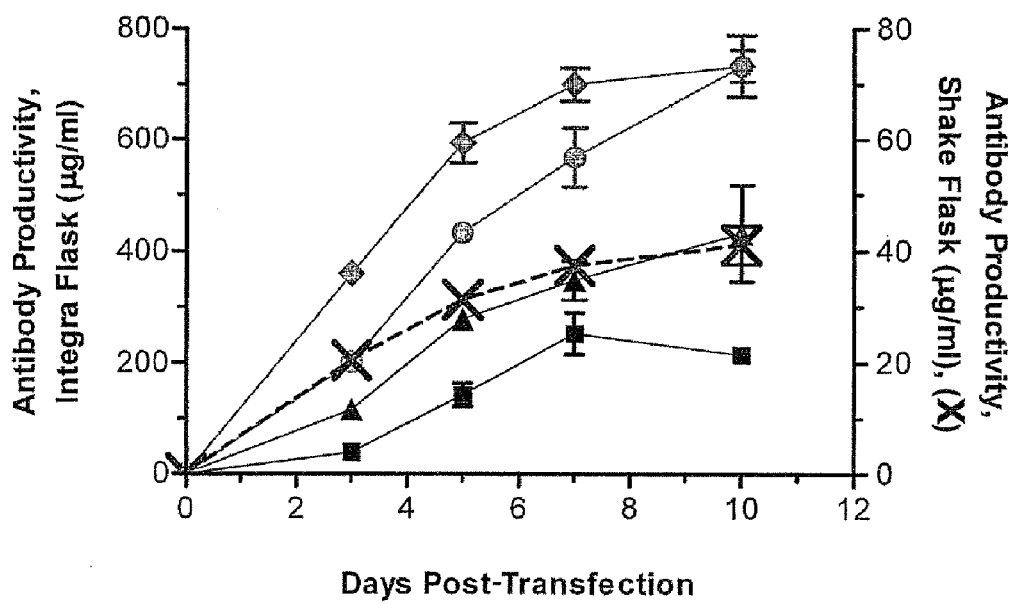
FIG. 8B is a graph of the concentration of antibody produced by cells transfected with DNA encoding Ab#2 as a function of time post-transfection. In both FIGS. 8A and 8B, ■ is I-50; ▲ is 1-100; • is I-200; ♦ is I-400; and × is E-200.
Figure 9A:
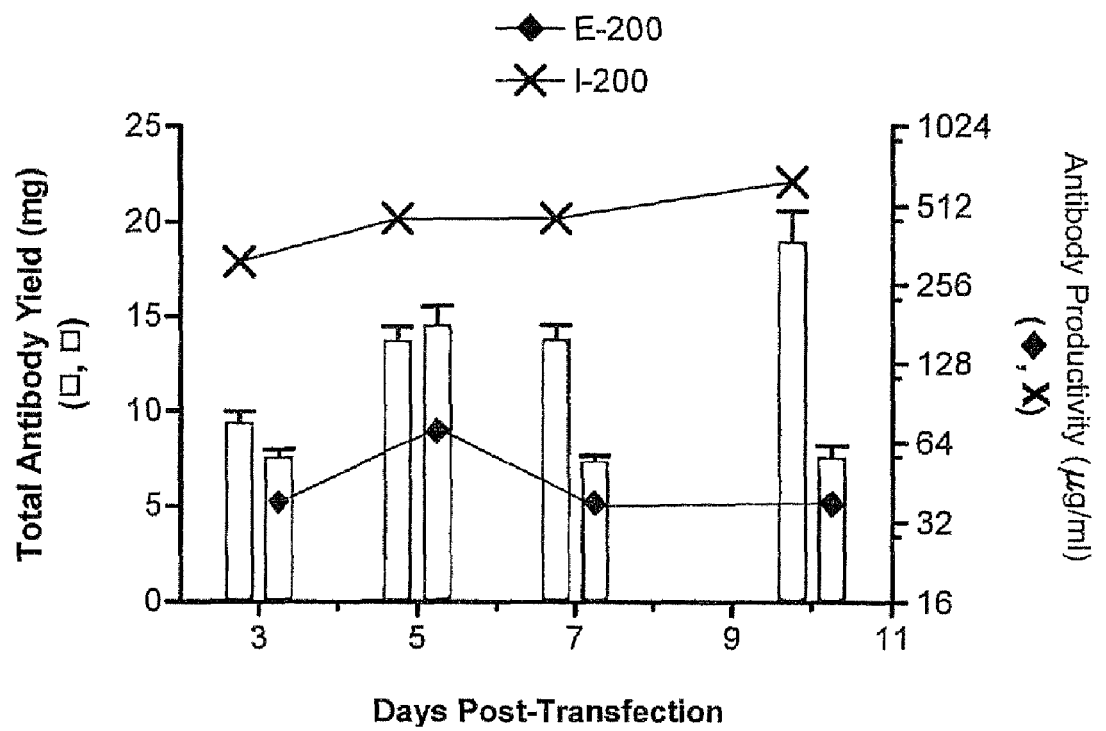
FIG. 9A is a graph of the total antibody produced by cells transfected with DNA encoding Ab#1 as a function of time post-transfection.
Figure 9B:
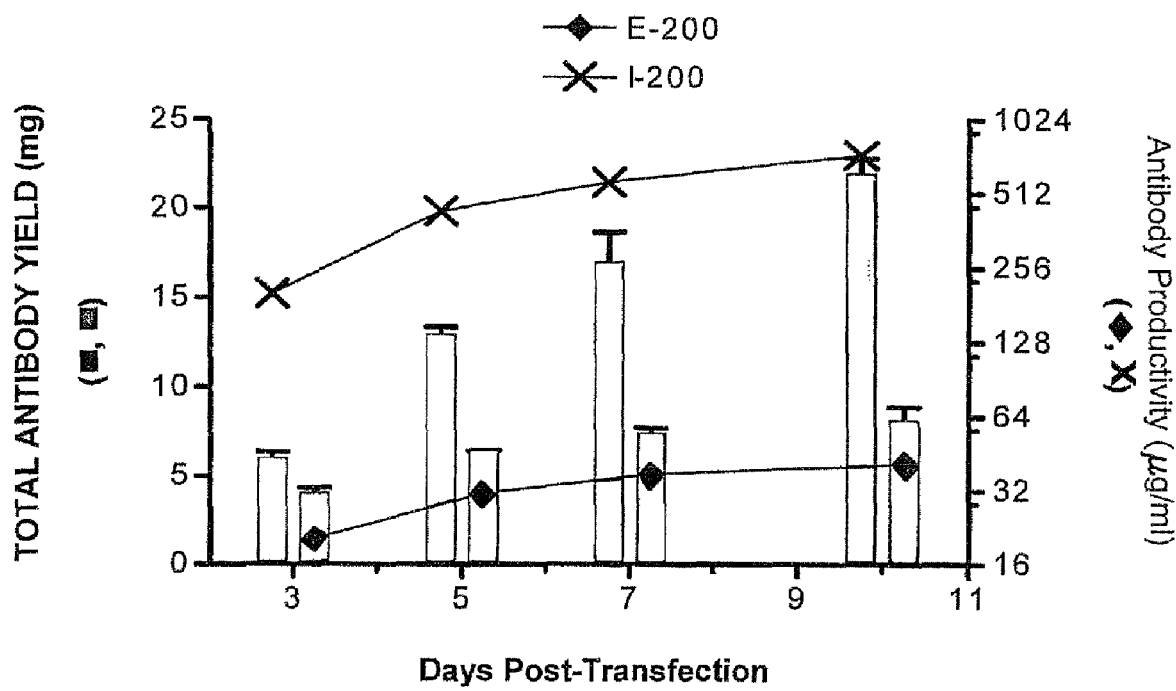
FIG. 9B is a graph of the total yield of antibody produced by cells transfected with DNA encoding Ab#2 as a function of time post-transfection.

As shown in FIGS. 8A and 8B, antibody productivity for the two antibodies tested, Ab#1 and Ab#2, were different in Erlenmeyer flasks. Ab#1 peaked early at day 5 (~70 μg/ml), followed by a decrease in antibody concentration. Ab#2 showed slower and steadier productivity over the full 10 days, achieving a maximal antibody output of ~40 μg/ml. For both Ab#1 and Ab#2, antibody productivity in the Integra flasks achieved steady levels of increasing Ab productivity over the 10 day period. An exception was the I-400 sample for Ab#1, which showed slight decreases in productivity at days 7 and 10; however, the decrease was substantially less as compared to that in the E-200 samples.

As shown in Table 2, the maximal yield for Ab#1 in the E-200 culture was ~15 mg at day 5. Comparable levels (≧90% of E-200 maximum) were obtained in the I-200 and I-400 cultures at day 5 as well, and higher total yields were obtained with I-100 and I-200 after day 10, namely 166% (24 mg) and 131% (19 mg), respectively.

As also shown in Table 2, the maximal yield for Ab#2 in the E-200 culture was ~8 mg at day 10. Comparable levels (>90% of E-200 maximum) were obtained as early as day 3 with I-400 (~11 mg), at day 5 with I-100 and I-200 (8 mg and 13 mg, respectively), and day 7 with I-50 (8 mg). Higher yields were obtained for I-100, I-200, and I-400 at day 10, 157% (13 mg), 268% (22 mg), and 268% (22 mg), respectively.

The results of this example demonstrated high levels of antibody production in Integra flasks within short periods of time. Cell densities of $1.0 \times 10^6$ and $1.5 \times 10^7$ were examples of optimal densities for producing high levels of antibodies. As shown herein, transiently transfected cells, for example, 293E cells, in membrane-enhancing culturing vessels such as Integra flasks, generated higher total antibody yields over cells cultured in Erlenmeyer flasks, irrespective of antibody productivity levels in shake cultures. Transiently expressing antibodies in membrane-enhancing culturing vessels such as Integra flasks also appeared to better retain antibody stability upon exhaustion of the culture.

As shown by the results obtained herein, total antibody yields from transiently transfected 293E cells are significantly increased when cultured in Integra flasks vs. standard Erlenmeyer flasks. Increasing the number of transfected cells seeded in the Integra flask can substantially decrease the time to reach maximum antibody yield, while decreasing the seeding density allows for multi-mg production of antibodies using a fraction of the cells under normal conditions in an Erlenmeyer flask. Generating transiently expressed antibodies in Integra flasks also better maintains the antibody titer for longer periods of time thus allowing for greater confidence to allow cultures to proceed to extinction without significant loss of antibody. Advantageously, usage of membrane-enhancing culturing vessels, such as Integra flasks, for transient protein production, such as antibody production, allows for increased total yield, faster production by using more cells, and/or conservation of cells by using fewer cells while maintaining productivity comparable to non-membrane culturing vessels, such as Erlenmeyer flasks.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of producing a recombinant antibody or antigen-binding fragment thereof, the method comprising contacting human embryonic kidney cells in a medium with a first vector and a second vector, wherein
   (a) the first vector encodes a heavy chain of an immunoglobulin, or a functional fragment thereof and the second vector encodes a light chain of the immunoglobulin, or a functional fragment thereof, wherein the functional fragments thereof are capable of forming an antigen-binding fragment of the immunoglobulin,
   (b) each of the first vector and the second vector comprises a 3' untranslated region (UTR) of a light chain gene and an oriP, wherein the 3'UTR comprises a nucleotide sequence of nucleotides 1062-2560 of SEQ ID NO: 1,
   (c) the heavy chain or functional fragment thereof encoded by the first vector and the light chain or functional fragment thereof encoded by the second vector are each expressed from a promoter that is the same for each of the first and second vectors, and
   (d) the second vector is present in the medium in an amount which is about 1.5 to 2.5 times as much as the amount of the first vector, whereupon a recombinant antibody or antigen-binding fragment thereof is produced.

2. The method of claim 1, wherein the second vector is present in the medium in an amount which is about 1.75 to 2.25 times as much as the amount of the first vector.

3. The method of claim 2, wherein the second vector is present in the medium in an amount which is about twice as much as the amount of the first vector.

4. The method of claim 1, wherein each of the first vector and the second vector is a recombinant transient expression vector.

5. The method of claim 1, wherein the promoter of each of the first vector and the second vector is a viral promoter.

6. The method of claim 5, wherein the viral promoter is a CMV promoter.

7. The method of claim 1, wherein each of the first vector and the second vector comprises the 5'UTR intron nucleotides 888-974 of SEQ ID NO: 1.

8. The method of claim 1, wherein each of the first vector and second vector comprises an antibody signal sequence.

9. The method of claim 1, wherein the cells are contacted with the first vector and second vector simultaneously.

10. The method of claim 1, wherein the cells are contacted with the first vector and second vector in the presence of a cationic polymer.

11. The method of claim 10, wherein the cationic polymer is polyethyleneimine (PEI).

12. The method of claim 11, wherein the PEI is a linear PEI.

13. The method of claim 12, wherein the linear PEI is present in an amount that is about 1.5 to 4.5 times the amount of the first vector and second vector.

14. The method of claim 13, wherein the linear PEI is present in an amount that is about 2.5 to 3.5 times the amount of the first vector and second vector.

15. The method of claim 14, wherein the linear PEI is present in an amount that is about twice the amount of the first vector and second vector.

16. The method of claim 1, wherein the human embryonic kidney cells express Epstein-Barr virus nuclear antigen-1 protein (EBNA-1).

17. The method of claim 16, wherein the cells are 293E cells.

18. The method of claim 1 further comprising isolating the cells from the medium and culturing the cells in a second medium in a membrane-enhanced culturing vessel, wherein the second medium is different from the medium.

19. The method of claim 18, wherein the second medium is a serum-free cell culture medium.

20. The method of the claim 18 further comprising purifying the recombinant antibody or antigen-binding fragment thereof from the second medium.

21. The method of claim 20, wherein the purifying comprises centrifuging the second medium through a column comprising Protein A.

22. The method of claim 20, wherein the purifying occurs after 3 days of culturing the cells in the second medium.

23. The method of claim 20, wherein the purifying occurs after 7 days of culturing the cells in the second medium.

24. The method of claim 22, wherein at least 300 μg/ml recombinant antibody or antigen-binding fragment thereof is produced in the second medium.

25. The method of claim 24, wherein at least 500 μg/ml recombinant antibody or antigen-binding fragment thereof is produced in the second medium.

26. The method of claim 25, wherein at least 700 μg/ml recombinant antibody or antigen-binding fragment thereof is produced in the second medium.

27. The method of claim 18, wherein the culturing comprises seeding cells in the second medium at a cell density between about $1.0 \times 10^6$ and $2.0 \times 10^7$ cells/ml.

28. The method of claim 27, wherein the cell density is about $3.0 \times 10^6$ to about $1.0 \times 10^7$ cells/ml.

29. The method of claim 1, comprising culturing the cells, which have been contacted with the first vector and the second vector in a medium in a membrane-enhanced culturing vessel or in a Fernbach flask, whereupon the recombinant antibody or antigen-binding fragment thereof is produced.

30. The method of claim 29, wherein the medium is a serum-free cell culture medium.

31. The method of claim 29, wherein the method further comprises purifying the recombinant antibody or antigen-binding fragment thereof from the medium.

32. The method of claim 31, wherein the purifying comprises centrifuging the medium through a column comprising Protein A.

33. The method of claim 31, wherein the purifying occurs after 3 days of culturing the cells in the medium.

34. The method of claim 31, wherein the purifying occurs after 7 days of culturing the cells in the medium.

35. The method of claim 1, wherein the heavy chain is a human heavy chain.

36. The method of claim 1, wherein the light chain is a human light chain.

* * * * *

SEQUENCE LISTING

<160> NUMBER OF SEQ ID NOS: 17

<210> SEQ ID NO 1
<211> LENGTH: 7006
<212> TYPE: DNA
<213> ORGANISM: Epstein Barr virus

<400> SEQUENCE: 1

```
aagcttgagt tttatgggtg gcagtcactg gctggctagg cacatagcca ggccaaacct      60
aggcctccaa gggctcccca aaatctgaat ttctgagtag tcttcatccc ctctcctgct     120
ctaaggtcag gtccatcctc tctggtcctt accttgatga caaggatcga cattgattat     180
tgactagtta ttaatagtaa tcaattacgg ggtcattagt tcatagccca tatatggagt     240
tccgcgttac ataacttacg gtaaatggcc cgcctggctg accgcccaac gaccccccgcc    300
cattgacgtc aataatgacg tatgttccca tagtaacgcc aatagggact ttccattgac     360
gtcaatgggt ggagtattta cggtaaactg cccacttggc agtacatcaa gtgtatcata     420
tgccaagtac gccccctatt gacgtcaatg acggtaaatg gcccgcctgg cattatgccc     480
agtacatgac cttatgggac tttcctactt ggcagtacat ctacgtatta gtcatcgcta     540
ttaccatggt gatgcggttt tggcagtaca tcaatgggcg tggatagcgg tttgactcac     600
ggggatttcc aagtctccac cccattgacg tcaatgggag tttgttttgg caccaaaatc     660
aacgggactt tccaaaatgt cgtaacaact ccgccccatt gacgcaaatg ggcggtaggc     720
gtgtacggtg ggaggtctat ataagcagag ctcgtttagt gaaccgtcag atcgcctgga     780
gacgccatcc acgctgtttt gacctccata gaagacaccg ggaccgatcc agcctccgcg     840
gccgggaacg gtgcattgga acgcggattc cccgtgccaa gagtgacgta agtaccgcct     900
atagagtcta taggcccacc cccttggctt cttatggatc cggtggtggt gcaaatcaaa     960
gaactgctcc tcagtggatg ttgcctttac ttctaggcct gtacggaagt gttacttctg    1020
ctctaaaagc tgctgcaggt cgacgaattc atcgatgata tctcgagccc gcccgtcaca    1080
aagagcttca acagggggaga gtgttagagg gagaagtgcc cccacctgct cctcagttcc    1140
agcctgaccc cctcccatcc tttggcctct gacccttttt ccacagggga cctacccccta  1200
ttgcggtcct ccagctcatc tttcacctca cccccctcct cctccttggc tttaattatg    1260
ctaatgttgg aggagaatga ataaataaag tgaatctttg cacctgtggt ttctctcttt    1320
cctcactaga ggatctctgt cttttcttact aaatggtagt aatcagttgt ttttccagtt    1380
acctgggttt ctcttctaaa gaagttaaat gtttagttgc cctgaaatcc accacactta    1440
aaggataaat aaaaccctcc acttgccctg gttggctgtc cactacatgg cagtcctttc    1500
taaggttcac gagtactatt catggcttat ttctctgggc catggtaggt ttgaggaggc    1560
atacttccta gttttcttcc cctaagtcgt caaagtcctg aaggggggaca gtctttacaa    1620
gcacatgttc tgtaatctga ttcaacctac ccagtaaact tggcgaagca gtagaatcat    1680
tatcacagga agcaaaggca acctaaatgt gcaagcaata ggaaaatgtg gaagcccatc    1740
```

```
atagtacttg gacttcatct gcttttgtgc cttcactaag ttttttaaaca tgagctggct   1800 cctatctgcc attggcaagg ctgggcacta cccacaacct acttcaagga cctctatacc   1860
gtgagattac acacatacat caaaatttgg gaaaagttct accaagctga gagctgatca   1920
ccccactctt aggtgcttat ctctgtacac cagaaacctt aagaagcaac cagtattgag   1980
agactcattt atgaaagtct aaaactggat acaaccaaaa tgtccaccaa cagttaaatt   2040
atgacatgtt cacaattgag ctattactta ataaggagaa ttaataaaat aaaacttaag   2100
agcatagttt aatctcataa acaagataat aagcaaaaca aaacattttt tcatccatgt   2160
aagtttaaaa gcaggtaaaa tttaaaatta agagagacat aagttttgag gtagcaagat   2220
ggaaactctg gggcttgggg aatgttctgt ctctctgtat gggatgtgaa agttactatt   2280
gtggaattgg gatctatgtt cttcctgtat atattgtata cttcataata acttcaccta   2340
aagaaatatc taatacccag tgcatacata aaagaggata caaggaatga atcatacgtc   2400
aaggccagaa agacaataaa gtaggggatc cagacatgat aagatacatt gatgagtttg   2460
gacaaaccac aactagaatg cagtgaaaaa aatgctttat ttgtgaaatt tgtgatgcta   2520
ttgctttatt tgtaaccatt ataagctgca ataaacaagt tctctagatg tgtaactctt   2580
ggctgaagct cttacaccaa tgctggggga catgtacctc ccaggggccc aggaagacta   2640
cgggaggcta caccaacgtc aatcagaggg gcctgtgtag ctaccgataa gcggaccctc   2700
aagagggcat tagcaatagt gttttataagg ccccccttgtt aaccctaaac gggtagcata   2760
tgcttcccgg gtagtagtat atactatcca gactaaccct aattcaatag catatgttac   2820
ccaacgggaa gcatatgcta tcgaattagg gttagtaaaa gggtcctaag gaacagcgat   2880
atctcccacc ccatgagctg tcacggtttt atttacatgg ggtcaggatt ccacgagggt   2940
agtgaaccat tttagtcaca agggcagtgg ctgaagatca aggagcgggc agtgaactct   3000
cctgaatctt cgcctgcttc ttcattctcc ttcgtttagc taatagaata actgctgagt   3060
tgtgaacagt aaggtgtatg tgaggtgctc gaaaacaagg tttcaggtga cgcccccaga   3120
ataaaatttg gacgggggt tcagtggtgg cattgtgcta tgacaccaat ataaccctca   3180 caaaccccctt gggcaataaa tactagtgta ggaatgaaac attctgaata tctttaacaa   3240
tagaaatcca tggggtgggg acaagccgta aagactggat gtccatctca cacgaattta   3300
tggctatggg caacacataa tcctagtgca atatgatact ggggttatta agatgtgtcc   3360
caggcaggga ccaagacagg tgaaccatgt tgttacactc tatttgtaac aaggggaaag   3420
agagtggacg ccgacagcag cggactccac tggttgtctc taacacccccc gaaaattaaa   3480 cggggctcca cgccaatggg gcccataaac aaagacaagt ggccactctt ttttttgaaa   3540
ttgtggagtg ggggcacgcg tcagccccca cacgccgccc tgcggttttg gactgtaaaa   3600
taagggtgta ataacttggc tgattgtaac cccgctaacc actgcggtca aaccacttgc   3660
ccacaaaacc actaatggca ccccggggaa tacctgcata gtaggtgggg cgggccaaga   3720 tagggggcgcg attgctgcga tctggaggac aaattacaca cacttgcgcc tgagcgccaa   3780
gcacagggtt gttggtcctc atattcacga ggtcgctgag agcacggtgg gctaatgttg   3840
ccatgggtag catatactac ccaaatatct ggatagcata tgctatccta atctatatct   3900
gggtagcata ggctatccta atctatatct gggtagcata tgctatccta atctatatct   3960
gggtagtata tgctatccta atttatatct gggtagcata ggctatccta atctatatct   4020
gggtagcata tgctatccta atctatatct gggtagtata tgctatccta atctgtatcc   4080
gggtagcata tgctatccta atagagatta gggtagtata tgctatccta atttatatct   4140
```

```
gggtagcata tactacccaa atatctggat agcatatgct atcctaatct atatctgggt      4200
agcatatgct atcctaatct atatctgggt agcataggct atcctaatct atatctgggt      4260
agcatatgct atcctaatct atatctgggt agtatatgct atcctaattt atatctgggt      4320
agcataggct atcctaatct atatctgggt agcatatgct atcctaatct atatctgggt      4380
agtatatgct atcctaatct gtatccgggt agcatatgct atcctcatgc atatacagtc      4440
agcatatgat acccagtagt agagtgggag tgctatcctt tgcatatgcc gccacctccc      4500
aagggggcgt gaattttcgc tgcttgtcct tttcctgctg gttggcatgc cggggagagg      4560
cggtttgcgt attgggcgct cttccgcttc ctcgctcact gactcgctgc gctcggtcgt      4620
tcggctgcgg cgagcggtat cagctcactc aaaggcggta atacggttat ccacagaatc      4680 agggataac gcaggaaaga acatgtgagc aaaaggccag caaaaggcca ggaaccgtaa      4740
aaaggccgcg ttgctggcgt ttttccatag gctccgcccc cctgacgagc atcacaaaaa      4800
tcgacgctca agtcagaggt ggcgaaaccc gacaggacta taaagatacc aggcgtttcc      4860
ccctggaagc tccctcgtgc gctctcctgt tccgaccctg ccgcttaccg gatacctgtc      4920
cgcctttctc ccttcgggaa gcgtggcgct ttctcatagc tcacgctgta ggtatctcag      4980
ttcggtgtag tcgttcgct ccaagctggg ctgtgtgcac gaaccccccg ttcagcccga      5040
ccgctgcgcc ttatccggta actatcgtct tgagtccaac ccggtaagac acgacttatc      5100
gccactggca gcagccactg gtaacaggat tagcagagcg aggtatgtag gcggtgctac      5160
agagttcttg aagtggtggc ctaactacgg ctacactaga agaacagtat ttggtatctg      5220
cgctctgctg aagccagtta ccttcggaaa aagagttggt agctcttgat ccggcaaaca      5280
aaccaccgct ggtagcggtg gtttttttgt ttgcaagcag cagattacgc gcagaaaaaa      5340
aggatctcaa gaagatcctt tgatcttttc tacggggtct gacgctcagt ggaacgaaaa      5400
ctcacgttaa gggattttgg tcatgagatt atcaaaaagg atcttcacct agatcctttt      5460
aaattaaaaa tgaagtttta aatcaatcta agtatatat gagtaaactt ggtctgacag      5520
ttaccaatgc ttaatcagtg aggcacctat ctcagcgatc tgtctatttc gttcatccat      5580
agttgcctga ctccccgtcg tgtagataac tacgatacgg agggcttac catctggccc      5640 cagtgctgca atgataccgc gagacccacg ctcaccggct ccagatttat cagcaataaa      5700
ccagccagcc ggaagggccg agcgcagaag tggtcctgca actttatccg cctccatcca      5760
gtctattaat tgttgccggg aagctagagt aagtagttcg ccagttaata gtttgcgcaa      5820
cgttgttgcc attgctacag gcatcgtggt gtcacgctcg tcgtttggta tggcttcatt      5880
cagctccggt tcccaacgat caaggcgagt tacatgatcc cccatgttgt gcaaaaaagc      5940
ggttagctcc ttcggtcctc cgatcgttgt cagaagtaag ttggccgcag tgttatcact      6000
catggttatg gcagcactgc ataattctct tactgtcatg ccatccgtaa gatgcttttc      6060
tgtgactggt gagtactcaa ccaagtcatt ctgagaatag tgtatgcggc gaccgagttg      6120
ctcttgcccg gcgtcaatac gggataatac cgcgccacat agcagaactt taaaagtgct      6180
catcattgga aaacgttctt cggggcgaaa actctcaagg atcttaccgc tgttgagatc      6240
cagttcgatg taacccactc gtgcacccaa ctgatcttca gcatctttta ctttcaccag      6300
cgtttctggg tgagcaaaaa caggaaggca aaatgccgca aaaagggaa taagggcgac      6360 acggaaatgt tgaatactca tactcttcct ttttcaatat tattgaagca tttatcaggg      6420
ttattgtctc atgagcggat acatatttga atgtatttag aaaaataaac aatagggggt      6480
```

-continued

```
tccgcgcaca tttccccgaa aagtgccacc tgacgtctaa gaaaccgcgg ccgcaacaga      6540
cgtctaagaa accattatta tcatgacatt aacctataaa aataggcgta tcacgaggcc      6600
ctttcgtctc gcgcgtttcg gtgatgacgg tgaaaacctc tgacacatgc agctcccgga      6660
gacggtcaca gcttgtctgt aagcggatgc cgggagcaga caagcccgtc agggcgcgtc      6720
agcgggtgtt ggcgggtgtc ggggctggct taactatgcg gcatcagagc agattgtact      6780
gagagtgcac catatgcggt gtgaaatacc gcacagatgc gtaaggagaa aataccgcat      6840
caggcgccat tcgccattca ggctgcgcaa ctgttgggaa gggcgatcgg tgcgggcctc      6900
ttcgctatta cgccagctgg cgaaagggg  atgtgctgca aggcgattaa gttgggtaac      6960
gccagggttt tcccagtcac gacgttgtaa aacgacggcc agtgcc                     7006
```

<210> SEQ ID NO 2
<211> LENGTH: 57
<212> TYPE: DNA
<213> ORGANISM: Homo Sapiens
<220> FEATURE:
<221> NAME/KEY: misc_feature
<223> OTHER INFORMATION: Signal Sequence
<220> FEATURE:
<221> NAME/KEY: CDS
<222> LOCATION: (1)..(57)

<400> SEQUENCE: 2

```
atg gga tgg agc tgt atc atc ctc ttc ttg gta gca aca gct aca ggt       48
Met Gly Trp Ser Cys Ile Ile Leu Phe Leu Val Ala Thr Ala Thr Gly
1               5                   10                  15 gtc cac tcc                                                             57
Val His Ser
```

<210> SEQ ID NO 3
<211> LENGTH: 19
<212> TYPE: PRT
<213> ORGANISM: Homo Sapiens

<400> SEQUENCE: 3

```
Met Gly Trp Ser Cys Ile Ile Leu Phe Leu Val Ala Thr Ala Thr Gly
1               5                   10                  15

Val His Ser
```

<210> SEQ ID NO 4
<211> LENGTH: 993
<212> TYPE: DNA
<213> ORGANISM: Homo Sapiens
<220> FEATURE:
<221> NAME/KEY: misc_feature
<223> OTHER INFORMATION: Heavy Chain Gamma 1
<220> FEATURE:
<221> NAME/KEY: CDS
<222> LOCATION: (1)..(993)

<400> SEQUENCE: 4

```
gcc agc aca aag ggc cca tcg gtc ttc ccc ctg gca ccc tcc tcc aag       48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac       96
Ser Thr Ser Gly Gly Thr Ala Ala Leu Gly Cys Leu Val Lys Asp Tyr
                20                  25                  30 ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
            35                  40                  45 ggc gtg cac acc ttc ccg gct gtc cta cag tcc tca gga ctc tac tcc      192
```

```
Gly Val His Thr Phe Pro Ala Val Leu Gln Ser Ser Gly Leu Tyr Ser
 50                  55                  60 ctc agc agc gtg gtg acc gtg ccc tcc agc agc ttg ggc acc cag acc      240
Leu Ser Ser Val Val Thr Val Pro Ser Ser Ser Leu Gly Thr Gln Thr
 65                  70                  75                  80 tac atc tgc aac gtg aat cac aag ccc agc aac acc aag gtg gac aag      288
Tyr Ile Cys Asn Val Asn His Lys Pro Ser Asn Thr Lys Val Asp Lys
                 85                  90                  95 aga gtt gag ccc aaa tct tgt gac aaa act cac aca tgt cca ccg tgc      336
Arg Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca      384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc      432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg      480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag      528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg      576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac      624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg      672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gag gag      720
Gln Pro Arg Glu Pro Gln Val Tyr Thr Leu Pro Pro Ser Arg Glu Glu
225                 230                 235                 240 atg acc aag aac cag gtc agc ctg acc tgc ctg gtc aaa ggc ttc tat      768
Met Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac      816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc      864
Asn Tyr Lys Thr Thr Pro Pro Val Leu Asp Ser Asp Gly Ser Phe Phe
        275                 280                 285 ctc tat agc aag ctc acc gtg gac aag agc agg tgg cag cag ggg aac      912
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320 cag aag agc ctc tcc ctg tcc ccg ggt aaa tga                          993
Gln Lys Ser Leu Ser Leu Ser Pro Gly Lys
                325                 330

<210> SEQ ID NO 5
<211> LENGTH: 330
<212> TYPE: PRT
<213> ORGANISM: Homo Sapiens

<400> SEQUENCE: 5
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 6
<211> LENGTH: 981
<212> TYPE: DNA
<213> ORGANISM: Homo Sapiens
<220> FEATURE:
<221> NAME/KEY: misc_feature
<223> OTHER INFORMATION: Heavy Chain Gamma 2
<220> FEATURE:
<221> NAME/KEY: CDS
<222> LOCATION: (1)..(981)

<400> SEQUENCE: 6

```
gcc agc aca aag ggc cca tcg gtc ttc ccc ctg gcg ccc tgc tcc agg    48
Ala Ser Thr Lys Gly Pro Ser Val Phe Pro Leu Ala Pro Cys Ser Arg
```

-continued

| | 1 | | | 5 | | | | 10 | | | | 15 | | | |
|---|---|---|---|---|---|---|---|---|---|---|---|---|---|---|---|

```
agc acc tcc gag agc aca gcg gcc ctg ggc tgc ctg gtc aag gac tac    96
Ser Thr Ser Glu Ser Thr Ala Ala Leu Gly Cys Leu Val Lys Asp Tyr
             20                  25                  30 ttc ccc gaa ccg gtg acg gtg tcg tgg aac tca ggc gct ctg acc agc   144
Phe Pro Glu Pro Val Thr Val Ser Trp Asn Ser Gly Ala Leu Thr Ser
         35                  40                  45 ggc gtg cac acc ttc ccg gct gtc cta cag tcc tca gga ctc tac tcc   192
Gly Val His Thr Phe Pro Ala Val Leu Gln Ser Ser Gly Leu Tyr Ser
     50                  55                  60 ctc agc agc gtg gtg acc gtg acc tcc agc aac ttc ggc acc cag acc   240
Leu Ser Ser Val Val Thr Val Thr Ser Ser Asn Phe Gly Thr Gln Thr
 65                  70                  75                  80 tac acc tgc aac gta gat cac aag ccc agc aac acc aag gtg gac aag   288
Tyr Thr Cys Asn Val Asp His Lys Pro Ser Asn Thr Lys Val Asp Lys
                 85                  90                  95 aca gtt gag cgc aaa tgt tgt gtc gag tgc cca ccg tgc cca gca cca   336
Thr Val Glu Arg Lys Cys Cys Val Glu Cys Pro Pro Cys Pro Ala Pro
             100                 105                 110 cct gtg gca gga ccg tca gtc ttc ctc ttc ccc cca aaa ccc aag gac   384
Pro Val Ala Gly Pro Ser Val Phe Leu Phe Pro Pro Lys Pro Lys Asp
         115                 120                 125 acc ctc atg atc tcc cgg acc cct gag gtc acg tgc gtg gtg gtg gac   432
Thr Leu Met Ile Ser Arg Thr Pro Glu Val Thr Cys Val Val Val Asp
     130                 135                 140 gtg agc cac gaa gac ccc gag gtc cag ttc aac tgg tac gtg gac ggc   480
Val Ser His Glu Asp Pro Glu Val Gln Phe Asn Trp Tyr Val Asp Gly
145                 150                 155                 160 atg gag gtg cat aat gcc aag aca aag cca cgg gag gag cag ttc aac   528
Met Glu Val His Asn Ala Lys Thr Lys Pro Arg Glu Glu Gln Phe Asn
                 165                 170                 175 agc acg ttc cgt gtg gtc agc gtc ctc acc gtc gtg cac cag gac tgg   576
Ser Thr Phe Arg Val Val Ser Val Leu Thr Val Val His Gln Asp Trp
             180                 185                 190 ctg aac ggc aag gag tac aag tgc aag gtc tcc aac aaa ggc ctc cca   624
Leu Asn Gly Lys Glu Tyr Lys Cys Lys Val Ser Asn Lys Gly Leu Pro
         195                 200                 205 gcc ccc atc gag aaa acc atc tcc aaa acc aaa ggg cag ccc cga gaa   672
Ala Pro Ile Glu Lys Thr Ile Ser Lys Thr Lys Gly Gln Pro Arg Glu
     210                 215                 220 cca cag gtg tac acc ctg ccc cca tcc cgg gag gag atg acc aag aac   720
Pro Gln Val Tyr Thr Leu Pro Pro Ser Arg Glu Glu Met Thr Lys Asn
225                 230                 235                 240 cag gtc agc ctg acc tgc ctg gtc aaa ggc ttc tac ccc agc gac atc   768
Gln Val Ser Leu Thr Cys Leu Val Lys Gly Phe Tyr Pro Ser Asp Ile
                 245                 250                 255 gcc gtg gag tgg gag agc aat ggg cag ccg gag aac aac tac aag acc   816
Ala Val Glu Trp Glu Ser Asn Gly Gln Pro Glu Asn Asn Tyr Lys Thr
             260                 265                 270 aca cct ccc atg ctg gac tcc gac ggc tcc ttc ttc ctc tac agc aag   864
Thr Pro Pro Met Leu Asp Ser Asp Gly Ser Phe Phe Leu Tyr Ser Lys
         275                 280                 285 ctc acc gtg gac aag agc agg tgg cag cag ggg aac gtc ttc tca tgc   912
Leu Thr Val Asp Lys Ser Arg Trp Gln Gln Gly Asn Val Phe Ser Cys
     290                 295                 300 tcc gtg atg cat gag gct ctg cac aac cac tac aca cag aag agc ctc   960
Ser Val Met His Glu Ala Leu His Asn His Tyr Thr Gln Lys Ser Leu
305                 310                 315                 320 tcc ctg tct ccg ggt aaa tga                                       981
```

```
Ser Leu Ser Pro Gly Lys
            325

<210> SEQ ID NO 7
<211> LENGTH: 326
<212> TYPE: PRT
<213> ORGANISM: Homo Sapiens

<400> SEQUENCE: 7

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 8
<211> LENGTH: 984
<212> TYPE: DNA
<213> ORGANISM: Homo Sapiens
```

```
<220> FEATURE:
<221> NAME/KEY: misc_feature
<223> OTHER INFORMATION: Heavy Chain Gamma 4
<220> FEATURE:
<221> NAME/KEY: CDS
<222> LOCATION: (1)..(984)

<400> SEQUENCE: 8 gcc agc aca aag ggc cca tcc gtc ttc ccc ctg gcg ccc tgc tcc agg      48
Ala Ser Thr Lys Gly Pro Ser Val Phe Pro Leu Ala Pro Cys Ser Arg
1               5                   10                  15 agc acc tcc gag agc aca gcc gcc ctg ggc tgc ctg gtc aag gac tac      96
Ser Thr Ser Glu Ser Thr Ala Ala Leu Gly Cys Leu Val Lys Asp Tyr
                20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
            35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
        50                  55                  60 ctc agc agc gtg gtg acc gtg ccc tcc agc agc ttg ggc acg aag acc     240
Leu Ser Ser Val Val Thr Val Pro Ser Ser Ser Leu Gly Thr Lys Thr
65                  70                  75                  80 tac acc tgc aac gta gat cac aag ccc agc aac acc aag gtg gac aag     288
Tyr Thr Cys Asn Val Asp His Lys Pro Ser Asn Thr Lys Val Asp Lys
                85                  90                  95 aga gtt gag tcc aaa tat ggt ccc cca tgc cca tca tgc cca gca cct     336
Arg Val Glu Ser Lys Tyr Gly Pro Pro Cys Pro Ser Cys Pro Ala Pro
                100                 105                 110 gag ttc ctg ggg gga cca tca gtc ttc ctg ttc ccc cca aaa ccc aag     384
Glu Phe Leu Gly Gly Pro Ser Val Phe Leu Phe Pro Pro Lys Pro Lys
            115                 120                 125 gac act ctc atg atc tcc cgg acc cct gag gtc acg tgc gtg gtg gtg     432
Asp Thr Leu Met Ile Ser Arg Thr Pro Glu Val Thr Cys Val Val Val
        130                 135                 140 gac gtg agc cag gaa gac ccc gag gtc cag ttc aac tgg tac gtg gat     480
Asp Val Ser Gln Glu Asp Pro Glu Val Gln Phe Asn Trp Tyr Val Asp
145                 150                 155                 160 ggc gtg gag gtg cat aat gcc aag aca aag ccg cgg gag gag cag ttc     528
Gly Val Glu Val His Asn Ala Lys Thr Lys Pro Arg Glu Glu Gln Phe
                165                 170                 175 aac agc acg tac cgt gtg gtc agc gtc ctc acc gtc ctg cac cag gac     576
Asn Ser Thr Tyr Arg Val Val Ser Val Leu Thr Val Leu His Gln Asp
                180                 185                 190 tgg ctg aac ggc aag gag tac aag tgc aag gtc tcc aac aaa ggc ctc     624
Trp Leu Asn Gly Lys Glu Tyr Lys Cys Lys Val Ser Asn Lys Gly Leu
            195                 200                 205 ccg tcc tcc atc gag aaa acc atc tcc aaa gcc aaa ggg cag ccc cga     672
Pro Ser Ser Ile Glu Lys Thr Ile Ser Lys Ala Lys Gly Gln Pro Arg
        210                 215                 220 gag cca cag gtg tac acc ctg ccc cca tcc cag gag gag atg acc aag     720
Glu Pro Gln Val Tyr Thr Leu Pro Pro Ser Gln Glu Glu Met Thr Lys
225                 230                 235                 240 aac cag gtc agc ctg acc tgc ctg gtc aaa ggc ttc tac ccc agc gac     768
Asn Gln Val Ser Leu Thr Cys Leu Val Lys Gly Phe Tyr Pro Ser Asp
                245                 250                 255 atc gcc gtg gag tgg gag agc aat ggg cag ccg gag aac aac tac aag     816
Ile Ala Val Glu Trp Glu Ser Asn Gly Gln Pro Glu Asn Asn Tyr Lys
                260                 265                 270 acc acg cct ccc gtg ctg gac tcc gac ggc tcc ttc ttc ctc tac agc     864
Thr Thr Pro Pro Val Leu Asp Ser Asp Gly Ser Phe Phe Leu Tyr Ser
```

```
                275                 280                 285
agg cta acc gtg gac aag agc agg tgg cag gag ggg aat gtc ttc tca      912
Arg Leu Thr Val Asp Lys Ser Arg Trp Gln Glu Gly Asn Val Phe Ser
    290                 295                 300 tgc tcc gtg atg cat gag gct ctg cac aac cac tac aca cag aag agc      960
Cys Ser Val Met His Glu Ala Leu His Asn His Tyr Thr Gln Lys Ser
305                 310                 315                 320 ctc tcc ctg tct ctg ggt aaa tga                                      984
Leu Ser Leu Ser Leu Gly Lys
                325
```

<210> SEQ ID NO 9
<211> LENGTH: 327
<212> TYPE: PRT
<213> ORGANISM: Homo Sapiens

<400> SEQUENCE: 9

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

```
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 10
<211> LENGTH: 318
<212> TYPE: DNA
<213> ORGANISM: Homo Sapiens
<220> FEATURE:
<221> NAME/KEY: misc_feature
<223> OTHER INFORMATION: Light Chain Kappa
<220> FEATURE:
<221> NAME/KEY: CDS
<222> LOCATION: (1)..(318)

<400> SEQUENCE: 10 gtg gct gca cca tct gtc ttc atc ttc ccg cca tct gat gag cag ttg      48
Val Ala Ala Pro Ser Val Phe Ile Phe Pro Pro Ser Asp Glu Gln Leu
1               5                   10                  15 aaa tct gga act gcc tct gtt gtg tgc ctg ctg aat aac ttc tat ccc      96
Lys Ser Gly Thr Ala Ser Val Val Cys Leu Leu Asn Asn Phe Tyr Pro
            20                  25                  30 aga gag gcc aaa gta cag tgg aag gtg gat aac gcc ctc caa tcg ggt     144
Arg Glu Ala Lys Val Gln Trp Lys Val Asp Asn Ala Leu Gln Ser Gly
        35                  40                  45 aac tcc cag gag agt gtc aca gag cag gac agc aag gac agc acc tac     192
Asn Ser Gln Glu Ser Val Thr Glu Gln Asp Ser Lys Asp Ser Thr Tyr
    50                  55                  60 agc ctc agc agc acc ctg acg ctg agc aaa gca gac tac gag aaa cac     240
Ser Leu Ser Ser Thr Leu Thr Leu Ser Lys Ala Asp Tyr Glu Lys His
65                  70                  75                  80 aaa gtc tac gcc tgc gaa gtc acc cat cag ggc ctg agc tcg ccc gtc     288
Lys Val Tyr Ala Cys Glu Val Thr His Gln Gly Leu Ser Ser Pro Val
                85                  90                  95 aca aag agc ttc aac agg gga gag tgt tag                             318
Thr Lys Ser Phe Asn Arg Gly Glu Cys
            100                 105

<210> SEQ ID NO 11
<211> LENGTH: 105
<212> TYPE: PRT
<213> ORGANISM: Homo Sapiens

<400> SEQUENCE: 11

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105

<210> SEQ ID NO 12
```

<211> LENGTH: 312
<212> TYPE: DNA
<213> ORGANISM: Homo Sapiens
<220> FEATURE:
<221> NAME/KEY: misc_feature
<223> OTHER INFORMATION: Light Chain Lambda
<220> FEATURE:
<221> NAME/KEY: CDS
<222> LOCATION: (1)..(312)

<400> SEQUENCE: 12

| aag | gcc | aac | ccc | act | gtc | act | ctg | ttc | ccg | ccc | tcc | tct | gag | gag | ctc | 48 |
| Lys | Ala | Asn | Pro | Thr | Val | Thr | Leu | Phe | Pro | Pro | Ser | Ser | Glu | Glu | Leu | |
| 1 | | | | 5 | | | | | 10 | | | | | 15 | | |

| caa | gcc | aac | aag | gcc | aca | cta | gtg | tgt | ctg | atc | agt | gac | ttc | tac | ccg | 96 |
| Gln | Ala | Asn | Lys | Ala | Thr | Leu | Val | Cys | Leu | Ile | Ser | Asp | Phe | Tyr | Pro | |
| | | | 20 | | | | | 25 | | | | | 30 | | | |

| gga | gct | gtg | aca | gtg | gcc | tgg | aag | gca | gat | ggc | agc | ccc | gtc | aag | gcg | 144 |
| Gly | Ala | Val | Thr | Val | Ala | Trp | Lys | Ala | Asp | Gly | Ser | Pro | Val | Lys | Ala | |
| | | 35 | | | | | 40 | | | | | 45 | | | | |

| gga | gtg | gag | acc | acc | aaa | ccc | tcc | aaa | cag | agc | aac | aac | aag | tac | gcg | 192 |
| Gly | Val | Glu | Thr | Thr | Lys | Pro | Ser | Lys | Gln | Ser | Asn | Asn | Lys | Tyr | Ala | |
| 50 | | | | | 55 | | | | | 60 | | | | | | |

| gcc | agc | agc | tac | ctg | agc | ctg | acg | ccc | gag | cag | tgg | aag | tcc | cac | aga | 240 |
| Ala | Ser | Ser | Tyr | Leu | Ser | Leu | Thr | Pro | Glu | Gln | Trp | Lys | Ser | His | Arg | |
| 65 | | | | 70 | | | | | 75 | | | | | 80 | | |

| agc | tac | agc | tgc | cag | gtc | acg | cat | gaa | ggg | agc | acc | gtg | gag | aag | aca | 288 |
| Ser | Tyr | Ser | Cys | Gln | Val | Thr | His | Glu | Gly | Ser | Thr | Val | Glu | Lys | Thr | |
| | | | 85 | | | | | 90 | | | | | 95 | | | |

| gtg | gcc | cct | aca | gaa | tgt | tca | tag | | | | | | | | | 312 |
| Val | Ala | Pro | Thr | Glu | Cys | Ser | | | | | | | | | | |
| | | 100 | | | | | | | | | | | | | | |

<210> SEQ ID NO 13
<211> LENGTH: 103
<212> TYPE: PRT
<213> ORGANISM: Homo Sapiens

<400> SEQUENCE: 13

Lys Ala Asn Pro Thr Val Thr Leu Phe Pro Pro Ser Ser Glu Glu Leu
1               5                   10                  15

Gln Ala Asn Lys Ala Thr Leu Val Cys Leu Ile Ser Asp Phe Tyr Pro
            20                  25                  30

Gly Ala Val Thr Val Ala Trp Lys Ala Asp Gly Ser Pro Val Lys Ala
        35                  40                  45

Gly Val Glu Thr Thr Lys Pro Ser Lys Gln Ser Asn Asn Lys Tyr Ala
    50                  55                  60

Ala Ser Ser Tyr Leu Ser Leu Thr Pro Glu Gln Trp Lys Ser His Arg
65                  70                  75                  80

Ser Tyr Ser Cys Gln Val Thr His Glu Gly Ser Thr Val Glu Lys Thr
                85                  90                  95

Val Ala Pro Thr Glu Cys Ser
            100

<210> SEQ ID NO 14
<211> LENGTH: 1410
<212> TYPE: DNA
<213> ORGANISM: HomoSapiens
<220> FEATURE:
<221> NAME/KEY: misc_feature
<223> OTHER INFORMATION: LDP-01 Heavy Chain
<220> FEATURE:
<221> NAME/KEY: misc_feature
<223> OTHER INFORMATION: heavy chain variable region sequence comprises
      amino acids 1-120
<220> FEATURE:
<221> NAME/KEY: misc_feature
<223> OTHER INFORMATION: heavy chain constant region sequences comprise
      amino acids 121-450
<220> FEATURE:
<221> NAME/KEY: misc_feature
<223> OTHER INFORMATION: signal sequence comprises amino acids -19 to -1
<220> FEATURE:
<221> NAME/KEY: CDS
<222> LOCATION: (1)..(1410)

<400> SEQUENCE: 14

```
atg gga tgg agc tgt atc atc ctc ttc ttg gta gca aca gct aca ggt        48
Met Gly Trp Ser Cys Ile Ile Leu Phe Leu Val Ala Thr Ala Thr Gly
1               5                   10                  15 gtc cac tcc cag gtc caa ctg cag gag agc ggt cca ggt ctt gtg aga        96
Val His Ser Gln Val Gln Leu Gln Glu Ser Gly Pro Gly Leu Val Arg
                20                  25                  30 cct agc cag acc ctg agc ctg acc tgc acc gtg tct ggc ttc acc ttc       144
Pro Ser Gln Thr Leu Ser Leu Thr Cys Thr Val Ser Gly Phe Thr Phe
            35                  40                  45 acc gat tac ctt ctg cac tgg gtg aga cag cca cct gga cga ggt ctt       192
Thr Asp Tyr Leu Leu His Trp Val Arg Gln Pro Pro Gly Arg Gly Leu
        50                  55                  60 gag tgg att gga tgg att gat cct gag gat ggt gaa aca aag tat ggt       240
Glu Trp Ile Gly Trp Ile Asp Pro Glu Asp Gly Glu Thr Lys Tyr Gly
65                  70                  75                  80 cag aag ttt caa agc aga gtg aca atg ctg gta gac acc agc aag aac       288
Gln Lys Phe Gln Ser Arg Val Thr Met Leu Val Asp Thr Ser Lys Asn
                85                  90                  95 cag ttc agc ctg aga ctc agc agc gtg aca gcc gcc gac acc gcg gtc       336
Gln Phe Ser Leu Arg Leu Ser Ser Val Thr Ala Ala Asp Thr Ala Val
                100                 105                 110 tat tat tgt gca aga ggc gaa tat aga tac aac tcg tgg ttt gat tac       384
Tyr Tyr Cys Ala Arg Gly Glu Tyr Arg Tyr Asn Ser Trp Phe Asp Tyr
            115                 120                 125 tgg ggt caa ggc tca cta gtc aca gtc tcc tca gcc tcc acc aag ggc       432
Trp Gly Gln Gly Ser Leu Val Thr Val Ser Ser Ala Ser Thr Lys Gly
        130                 135                 140 cca tcg gtc ttc ccc ctg gca ccc tcc tcc aag agc acc tct ggg ggc       480
Pro Ser Val Phe Pro Leu Ala Pro Ser Ser Lys Ser Thr Ser Gly Gly
145                 150                 155                 160 aca gcg gcc ctg ggc tgc ctg gtc aag gac tac ttc ccc gaa ccg gtg       528
Thr Ala Ala Leu Gly Cys Leu Val Lys Asp Tyr Phe Pro Glu Pro Val
                165                 170                 175 acg gtg tcg tgg aac tca ggc gcc ctg acc agc ggc gtg cac acc ttc       576
Thr Val Ser Trp Asn Ser Gly Ala Leu Thr Ser Gly Val His Thr Phe
                180                 185                 190 ccg gct gtc cta cag tcc tca gga ctc tac tcc ctc agc agc gtg gtg       624
Pro Ala Val Leu Gln Ser Ser Gly Leu Tyr Ser Leu Ser Ser Val Val
            195                 200                 205 acc gtg ccc tcc agc agc ttg ggc acc cag acc tac atc tgc aac gtg       672
Thr Val Pro Ser Ser Ser Leu Gly Thr Gln Thr Tyr Ile Cys Asn Val
        210                 215                 220 aat cac aag ccc agc aac acc aag gtg gac aag aaa gtt gag ccc aaa       720
Asn His Lys Pro Ser Asn Thr Lys Val Asp Lys Lys Val Glu Pro Lys
225                 230                 235                 240 tct tgt gac aaa act cac aca tgc cca ccg tgc cca gca cct gaa ctc       768
Ser Cys Asp Lys Thr His Thr Cys Pro Pro Cys Pro Ala Pro Glu Leu
                245                 250                 255
```

| | | | | | | | | | | | | | | | |
|---|---|---|---|---|---|---|---|---|---|---|---|---|---|---|---|
| gcg | ggg | gca | ccg | tca | gtc | ttc | ctc | ttc | ccc | cca | aaa | ccc | aag | cac | acc | 816 |
| Ala | Gly | Ala | Pro | Ser | Val | Phe | Leu | Phe | Pro | Pro | Lys | Pro | Lys | His | Thr | |
| | | | 260 | | | | 265 | | | | 270 | | | | | |

| | | | | | | | | | | | | | | | |
|---|---|---|---|---|---|---|---|---|---|---|---|---|---|---|---|
| ctc | atg | atc | tcc | cgg | acc | cct | gag | gtc | aca | tgc | gtg | gtg | gtg | gac | gtg | 864 |
| Leu | Met | Ile | Ser | Arg | Thr | Pro | Glu | Val | Thr | Cys | Val | Val | Val | Asp | Val | |
| | | 275 | | | | 280 | | | | 285 | | | | | | | agc cac gaa gac cct gag gtc aag ttc aac tgg tac gtg gac ggc gtg   912
Ser His Glu Asp Pro Glu Val Lys Phe Asn Trp Tyr Val Asp Gly Val
        290                 295                 300 gag gtg cat aat gcc aag aca aag ccg cgg gag gag cag tac aac agc   960
Glu Val His Asn Ala Lys Thr Lys Pro Arg Glu Glu Gln Tyr Asn Ser
305                 310                 315                 320 acg tac cgt gtg gtc agc gtc ctc acc gtc ctg cac cag gac tgg ctg  1008
Thr Tyr Arg Val Val Ser Val Leu Thr Val Leu His Gln Asp Trp Leu
                325                 330                 335 aat ggc aag gag tac aag tgc aag gtc tcc aac aaa gcc ctc cca gcc  1056
Asn Gly Lys Glu Tyr Lys Cys Lys Val Ser Asn Lys Ala Leu Pro Ala
            340                 345                 350 ccc atc gag aaa acc atc tcc aaa gcc aaa ggg cag ccc cga gaa cca  1104
Pro Ile Glu Lys Thr Ile Ser Lys Ala Lys Gly Gln Pro Arg Glu Pro
        355                 360                 365 cag gtg tac acc ctg ccc cca tcc cgg gat gag ctg acc aag aac cag  1152
Gln Val Tyr Thr Leu Pro Pro Ser Arg Asp Glu Leu Thr Lys Asn Gln
370                 375                 380 gtc agc ctg acc tgc ctg gtc aaa ggc ttc tat ccc agc gac atc gcc  1200
Val Ser Leu Thr Cys Leu Val Lys Gly Phe Tyr Pro Ser Asp Ile Ala
385                 390                 395                 400 gtg gag tgg gag agc aat ggg cag ccg gag aac aac tac aag acc acg  1248
Val Glu Trp Glu Ser Asn Gly Gln Pro Glu Asn Asn Tyr Lys Thr Thr
                405                 410                 415 cct ccc gtg ctg gac tcc gac ggc tcc ttc ttc ctc tac agc aag ctc  1296
Pro Pro Val Leu Asp Ser Asp Gly Ser Phe Phe Leu Tyr Ser Lys Leu
            420                 425                 430 acc gtg gac aag agc agg tgg cag cag ggg aac gtc ttc tca tgc tcc  1344
Thr Val Asp Lys Ser Arg Trp Gln Gln Gly Asn Val Phe Ser Cys Ser
        435                 440                 445 gtg atg cat gag gct ctg cac aac cac tac acg cag aag agc ctc tcc  1392
Val Met His Glu Ala Leu His Asn His Tyr Thr Gln Lys Ser Leu Ser
450                 455                 460 ctg tct ccg ggt aaa tga                                          1410
Leu Ser Pro Gly Lys
465

<210> SEQ ID NO 15
<211> LENGTH: 469
<212> TYPE: PRT
<213> ORGANISM: HomoSapiens

<400> SEQUENCE: 15

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Arg
            20                  25                  30

Pro Ser Gln Thr Leu Ser Leu Thr Cys Thr Val Ser Gly Phe Thr Phe
        35                  40                  45

Thr Asp Tyr Leu Leu His Trp Val Arg Gln Pro Pro Gly Arg Gly Leu
    50                  55                  60

Glu Trp Ile Gly Trp Ile Asp Pro Glu Asp Gly Glu Thr Lys Tyr Gly
65                  70                  75                  80

```
Gln Lys Phe Gln Ser Arg Val Thr Met Leu Val Asp Thr Ser Lys Asn
                85                  90                  95

Gln Phe Ser Leu Arg Leu Ser Ser Val Thr Ala Ala Asp Thr Ala Val
            100                 105                 110

Tyr Tyr Cys Ala Arg Gly Glu Tyr Arg Tyr Asn Ser Trp Phe Asp Tyr
        115                 120                 125

Trp Gly Gln Gly Ser Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Ala Gly Ala Pro Ser Val Phe Leu Phe Pro Pro Lys Pro Lys His Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 16
<211> LENGTH: 702
<212> TYPE: DNA
```

<213> ORGANISM: HomoSapiens
<220> FEATURE:
<221> NAME/KEY: misc_feature
<223> OTHER INFORMATION: LDP-01 Light Chain
<220> FEATURE:
<221> NAME/KEY: misc_feature
<223> OTHER INFORMATION: light chain variable region sequence comprises
      amino acids 1-109
<220> FEATURE:
<221> NAME/KEY: misc_feature
<223> OTHER INFORMATION: light chain constant region sequence comprises
      amino acids 110-214
<220> FEATURE:
<221> NAME/KEY: misc_feature
<223> OTHER INFORMATION: signal sequence comprises amino acids -19 to -1
<220> FEATURE:
<221> NAME/KEY: CDS
<222> LOCATION: (1)..(702)

<400> SEQUENCE: 16

```
atg gga tgg agc tgt atc atc ctc ttc ttg gta gca aca gct aca ggt      48
Met Gly Trp Ser Cys Ile Ile Leu Phe Leu Val Ala Thr Ala Thr Gly
1               5                   10                  15 gtc cac tcc gac atc cag atg acc cag agc cca agc agc ctg agc gcc      96
Val His Ser Asp Ile Gln Met Thr Gln Ser Pro Ser Ser Leu Ser Ala
            20                  25                  30 agc gtg ggt gac aga gtg acc atc acc tgt aaa gca agt aag agc att     144
Ser Val Gly Asp Arg Val Thr Ile Thr Cys Lys Ala Ser Lys Ser Ile
        35                  40                  45 agc aat tat tta gcc tgg tac cag cag aag cca ggt aag gct cca aag     192
Ser Asn Tyr Leu Ala Trp Tyr Gln Gln Lys Pro Gly Lys Ala Pro Lys
    50                  55                  60 ctg ctg atc tac tat ggg tca act ttg cga tct ggt gtg cca agc aga     240
Leu Leu Ile Tyr Tyr Gly Ser Thr Leu Arg Ser Gly Val Pro Ser Arg
65                  70                  75                  80 ttc agc ggt agc ggt agc ggt acc gac ttc acc ttc acc atc agc agc     288
Phe Ser Gly Ser Gly Ser Gly Thr Asp Phe Thr Phe Thr Ile Ser Ser
                85                  90                  95 ctc cag cca gag gac atc gcc acc tac tac tgc caa cag tat tat gaa     336
Leu Gln Pro Glu Asp Ile Ala Thr Tyr Tyr Cys Gln Gln Tyr Tyr Glu
            100                 105                 110 aga ccg ctc acg ttc ggc caa ggg acc aag gtg gaa atc aaa cga act     384
Arg Pro Leu Thr Phe Gly Gln Gly Thr Lys Val Glu Ile Lys Arg Thr
        115                 120                 125 gtg gct gca cca tct gtc ttc atc ttc ccg cca tct gat gag cag ttg     432
Val Ala Ala Pro Ser Val Phe Ile Phe Pro Pro Ser Asp Glu Gln Leu
    130                 135                 140 aaa tct gga act gcc tct gtt gtg tgc ctg ctg aat aac ttc tat ccc     480
Lys Ser Gly Thr Ala Ser Val Val Cys Leu Leu Asn Asn Phe Tyr Pro
145                 150                 155                 160 aga gag gcc aaa gta cag tgg aag gtg gat aac gcc ctc caa tcg ggt     528
Arg Glu Ala Lys Val Gln Trp Lys Val Asp Asn Ala Leu Gln Ser Gly
                165                 170                 175 aac tcc cag gag agt gtc aca gag cag gac agc aag gac agc acc tac     576
Asn Ser Gln Glu Ser Val Thr Glu Gln Asp Ser Lys Asp Ser Thr Tyr
            180                 185                 190 agc ctc agc agc acc ctg acg ctg agc aaa gca gac tac gag aaa cac     624
Ser Leu Ser Ser Thr Leu Thr Leu Ser Lys Ala Asp Tyr Glu Lys His
        195                 200                 205 aaa gtc tac gcc tgc gaa gtc acc cat cag ggc ctg agc tcg ccc gtc     672
Lys Val Tyr Ala Cys Glu Val Thr His Gln Gly Leu Ser Ser Pro Val
    210                 215                 220 aca aag agc ttc aac agg gga gag tgt tag                             702
Thr Lys Ser Phe Asn Arg Gly Glu Cys
```

-continued

```
225                 230

<210> SEQ ID NO 17
<211> LENGTH: 233
<212> TYPE: PRT
<213> ORGANISM: HomoSapiens

<400> SEQUENCE: 17

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Lys Ala Ser Lys Ser Ile
        35                  40                  45

Ser Asn Tyr Leu Ala Trp Tyr Gln Gln Lys Pro Gly Lys Ala Pro Lys
    50                  55                  60

Leu Leu Ile Tyr Tyr Gly Ser Thr Leu Arg Ser Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Gln Gln Tyr Tyr Glu
            100                 105                 110

Arg Pro Leu Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```